(12) United States Patent
Backman et al.

(10) Patent No.: US 10,684,417 B2
(45) Date of Patent: Jun. 16, 2020

(54) PROBE APPARATUS FOR MEASURING DEPTH-LIMITED PROPERTIES WITH LOW-COHERENCE ENHANCED BACKSCATTERING

(71) Applicants: NORTHWESTERN UNIVERSITY, Evanston, IL (US); AMERICAN BIOOPTICS, LLC, Chicago, IL (US)

(72) Inventors: Vadim Backman, Chicago, IL (US); Jeremy D. Rogers, Madison, WI (US); Nikhil N. Mutyal, Evanston, IL (US); Bradley Gould, Evanston, IL (US); Andrew J. Radosevich, Evanston, IL (US); The Quyen Nguyen, Evanston, IL (US)

(73) Assignees: NORTHWESTERN UNIVERSITY, Evanston, IL (US); AMERICAN BIOOPTICS, LLC, Chicago, IL (US)

( * ) Notice: Subject to any disclaimer, the term of this patent is extended or adjusted under 35 U.S.C. 154(b) by 0 days.

(21) Appl. No.: 15/886,431

(22) Filed: Feb. 1, 2018

(65) Prior Publication Data

US 2018/0180814 A1 Jun. 28, 2018

Related U.S. Application Data

(63) Continuation-in-part of application No. 13/963,560, filed on Aug. 9, 2013, now Pat. No. 9,885,834, which
(Continued)

(51) Int. Cl.
*G02B 6/26* (2006.01)
*G01N 21/47* (2006.01)
(Continued)

(52) U.S. Cl.
CPC ............ *G02B 6/262* (2013.01); *A61B 5/0066* (2013.01); *A61B 5/0084* (2013.01); *G01N 21/474* (2013.01); *G02B 6/3807* (2013.01)

(58) Field of Classification Search
CPC .......... G01J 3/02; G01J 3/0221; G01J 3/0224; G01J 3/4412; G01J 3/10; A61B 5/0084;
(Continued)

(56) References Cited

U.S. PATENT DOCUMENTS

| 5,037,202 A | 8/1991 | Batchelder et al. |
| 5,053,043 A | 10/1991 | Gottesman |

(Continued)

FOREIGN PATENT DOCUMENTS

| EP | 0286374 A2 | 10/1988 |
| JP | 10-506545 | 6/1998 |

(Continued)

OTHER PUBLICATIONS

Feb. 24, 2015 Office Action issued in European Application No. 10729602.2.
(Continued)

*Primary Examiner* — Michael P Mooney
(74) *Attorney, Agent, or Firm* — Nixon Peabody LLP

(57) ABSTRACT

Low-coherence enhanced backscattering (LEBS) spectroscopy is an angular resolved backscattering technique that is sensitive to sub-diffusion light transport length scales in which information about the scattering phase function is preserved. Lens-based and lens-free fiber optic LEBS probes are described that are capable of measuring optical properties of a target tissue through depth-limited measurements of backscattering angles within the enhanced backscattered cone.

19 Claims, 30 Drawing Sheets

Related U.S. Application Data is a continuation-in-part of application No. 12/684,837, filed on Jan. 8, 2010, now abandoned.

(60) Provisional application No. 61/143,407, filed on Jan. 8, 2009.

(51) Int. Cl.
*G02B 6/38* (2006.01)
*A61B 5/00* (2006.01)

(58) Field of Classification Search
CPC ... A61B 5/0261; A61B 5/0066; A61B 5/0075; A61B 5/0091; A61B 5/1459; G02B 6/04; G02B 6/06; G02B 6/241; G02B 6/26; G02B 6/262; G02B 6/32; G02B 6/36; G02B 6/3624; G02B 6/3807; G02B 6/3854; G02B 6/3855
USPC .. 385/12, 31, 33, 38, 39, 50, 53, 76–78, 81, 385/116, 117, 119, 136, 137, 139
See application file for complete search history.

(56) References Cited

U.S. PATENT DOCUMENTS

| | | | |
|---|---|---|---|
| 5,303,024 | A | 4/1994 | Thierman |
| 5,650,847 | A | 7/1997 | Maltsev et al. |
| 5,772,678 | A | 6/1998 | Thomason |
| 5,799,656 | A | 9/1998 | Alfano |
| 5,975,697 | A | 11/1999 | Podoleanu |
| 5,993,843 | A | 11/1999 | Sakurada |
| 6,035,229 | A | 3/2000 | Silverstein |
| 6,091,984 | A | 7/2000 | Perelman |
| 6,320,660 | B1 | 11/2001 | Ju |
| 6,381,018 | B1 | 4/2002 | Bigio |
| 6,404,497 | B1 | 6/2002 | Backman |
| 6,405,070 | B1 | 6/2002 | Banerjee |
| 6,485,413 | B1 | 11/2002 | Boppart |
| 6,556,853 | B1 | 4/2003 | Cabib |
| 6,624,890 | B2 | 9/2003 | Backman |
| 6,639,674 | B2 | 10/2003 | Sokolov |
| 6,650,357 | B1 | 11/2003 | Richardson |
| 6,912,412 | B2 | 6/2005 | Georgakoudi |
| 6,922,583 | B1 | 7/2005 | Perelman |
| 6,927,860 | B2 | 8/2005 | Podoleanu |
| 7,061,622 | B2 | 6/2006 | Rollins |
| 7,186,789 | B2 | 3/2007 | Hossainy |
| 7,652,772 | B2 | 1/2010 | Backman |
| 8,131,348 | B2 | 3/2012 | Backman |
| 2002/0135752 | A1 | 9/2002 | Sokolov |
| 2003/0036751 | A1 | 2/2003 | Anderson |
| 2003/0137669 | A1 | 7/2003 | Rollins |
| 2003/0191368 | A1 | 10/2003 | Wang |
| 2003/0215846 | A1 | 11/2003 | Watt |
| 2003/0232445 | A1 | 12/2003 | Fulghum |
| 2003/0236458 | A1 | 12/2003 | Hochman |
| 2004/0122341 | A1 | 6/2004 | Walsh |
| 2004/0147843 | A1 | 7/2004 | Bambot |
| 2004/0171567 | A1 | 9/2004 | Sidransky |
| 2004/0189987 | A1 | 9/2004 | Bondurant |
| 2004/0223162 | A1 | 11/2004 | Wax |
| 2004/0236186 | A1 | 11/2004 | Chu |
| 2004/0242976 | A1 | 12/2004 | Abreu |
| 2004/0249274 | A1 | 12/2004 | Yarovslovsky |
| 2005/0046821 | A1 | 3/2005 | Hanson |
| 2005/0265586 | A1 | 12/2005 | Rowe |
| 2006/0052709 | A1 | 3/2006 | DeBaryshe |
| 2006/0155178 | A1 | 7/2006 | Backman |
| 2006/0155195 | A1 | 7/2006 | Maier |
| 2006/0258909 | A1 | 11/2006 | Saadat |
| 2006/0293556 | A1 | 12/2006 | Garner |
| 2007/0078348 | A1 | 4/2007 | Holman |
| 2007/0129615 | A1 | 6/2007 | Backman |
| 2007/0173718 | A1 | 7/2007 | Richards-Kortum |
| 2007/0179368 | A1 | 8/2007 | Backman |
| 2007/0201033 | A1 | 8/2007 | Desjardins |
| 2007/0213591 | A1 | 9/2007 | Aizenfeld |
| 2008/0015569 | A1 | 1/2008 | Saadat |
| 2008/0037024 | A1* | 2/2008 | Backman ............... G01J 3/02 356/446 |
| 2008/0058622 | A1 | 3/2008 | Baker |
| 2008/0171989 | A1 | 7/2008 | Bell |
| 2008/0214940 | A1 | 9/2008 | Benaron |
| 2009/0075391 | A1* | 3/2009 | Fulghum, Jr. ...... A61B 1/00165 436/164 |
| 2009/0203977 | A1 | 8/2009 | Backman |
| 2009/0216075 | A1 | 8/2009 | Bell |
| 2009/0253967 | A1 | 10/2009 | Gill |
| 2011/0208273 | A1* | 8/2011 | Fortuna ................... A61N 5/06 607/89 |
| 2011/0230770 | A1 | 9/2011 | Furnish |
| 2013/0303861 | A1 | 11/2013 | Backman |

FOREIGN PATENT DOCUMENTS

| | | |
|---|---|---|
| JP | A-11-342123 | 12/1999 |
| JP | WO 2007/133684 | 11/2007 |
| WO | WO 2007/136880 | 11/2007 |

OTHER PUBLICATIONS

Dec. 2, 2014 Office Action issued in Chinese Patent Application No. 201080004243.2.

Sep. 8, 2014 Office Action issued in U.S. Appl. No. 12/684,837.

Jul. 10, 2014 Office Action issued in European Patent Application No. 10 729 602.2.

Final Rejection issued in U.S. Appl. No. 12/684,837 dated Feb. 5, 2014.

Georgakoudi, I., et al., "Trimodal Spectroscopy for the Detection and Characterization of Cervical Precaners in Vivo," Am. J. Obstet. Gynol., vol. 186, No. 3, Mar. 2002, pp. 374-382.

Aug. 6, 2013 Office Action issued in Japanese Application No. 2011/545475 (with English translation).

Jun. 20, 2013 Office Action issued in Chinese Patent Application No. 201080004243.2 (with English Translation).

Sep. 10, 2013 Office Action issued in U.S. Appl. No. 12/684,837.

Jun. 5, 2013 Extended European Search Report issued in European Application No. 10729602.2.

Backman, V. et al., "Polarized Light Scattering Spectroscopy for Quantitative Measurement of Epithelial Cellular Structurs in Situ," IEEE J. of Selected Topics in Quantum Electronics, vol. 5, No. 4, Jul./Aug. 1999, pp. 1019-1026.

Backman, V., "Measuring Cellular Structure at Submicrometer Scale With Light Scattering Spectroscopy," IEEE J. of Selected Topics in Quantum Electronics, vol. 7, No. 6, Nov./Dec. 2001, pp. 887-893.

Bigio, I.J. et al., "Ultraviolet and Visible Spectroscopies for Tissue Diagnostics: Flourescense Spectroscopy and elastic-Scattering Spectroscopy," Phys. Med. Bioi., vol. 42, 1997, pp. 803-814.

Cerussi, A.E. et al., "Spectroscopy Enhances the Information Content of Optical Mammography," J. of Biomed. Optics, vol. 7, No. 1, Jan. 2002, pp. 60-71.

Demos, S.G. et al., "Optical Polarization Imaging," Applied Optics, vol. 36, No. 1, Jan. 1, 1997, pp. 150-155.

Finlay, JC, et al., "Effect of Pigment Packaging on Diffuse Reflectance Spectroscopy of Samples Containing Red Blood Cells," Optics Letts., 29:9, May 1, 2004, pp. 965-967.

Georgakoudi, I. et al., "Imaging Human Epithelial Properties with Polarized Light Scattering Spectroscopy," Nature Medicine, vol. 7, No. 11, Nov. 2001, pp. 1245-1248.

Gurjar, R. et al., "Imaging Human Epithelial Properties with Polarized Light Scattering Spectroscopy," Nature Medicine, vol. 7, No. 11, Nov. 2001, pp. 1245-1248.

Horwitz, J. et al., "Micro-Architectural Alterations in Endoscopically Normal Mucosa Provides Accurate Risk Stratification for Colorectal Neoplasma," AJG Abstracts, vol. 99, No. 10, Undated, p. S326.

(56) References Cited

OTHER PUBLICATIONS

Jacques, S. et al., "Imaging Superficial Tissues with Polarized Light," Lasers in Surgery and Medicine, vol. 26, 2000, pp. 199-129.

Kim Y.L. et al., "Simultaneous Measurement of Angular and Spectral Properties of Light Scattering for Characterization of Tissue Microarchitecture and its Alteration in Early Precancer," IEEE Xplore Abstract, Jan. 23, 2009 (downloaded), published Oct. 27, 2003, 1 page.

Lin, Wei Chiang, et al., "Intraoperative Application of Optical Spectroscopy in the Presence of Blood," IEEE J. on Selected Topics in Quantum Electronics, vol. 7, No. 6, Nov./Dec. 2001, pp. 996-1003.

Liu, Y. et al., "Light scattering 'fingerprinting' for characterization of smooth muscle cell proliferation" Advanced Biomedical and Clinical Diagnostic Systems II. Edited by Cohn, Gerald E., et al. Proceedings of the SPIE, vol. 5319, pp. 32-40 (2004).

McDonald, D. et al., "Imaging of Angiogenesis: From Microscope to Clinic," Nature Medicine: Angiogenesis Focus, vol. 9, No. 6, Jun. 2003, pp. 713-725.

Mourant, J.R. et al., "Predications and Measurements of Scattering and Absorption Over Broad Wavelength Ranges in Tissue Phantoms," Applied Optics, vol. 36, No. 4, Feb. 1, 1997, pp. 949-957.

Muller, M.G. et al., "Spectroscopic Detection and Evaluation of Morphologic and Biochemical Changes in Early Human Oral Carcinoma," American Cancer Society, 2003, pp. 1681-1692.

Roy, Hermant K., "Down-regulation of SNAIL Supresses MIN Mouse Tumorigenesis," Mol. Cancer Ter., vol. 3, No. 9, Sep. 2004, pp. 1159-1165.

Roy, Hermant K. et al., "Spectral markers in Preneoplastic Intestinal Mucosa," Cancer Epidermol Biomarkers Pre v, vol. 14, No. 7, Jul. 2005, PD. 1639-1645.

Roy, Hermant K. et al., "Four Dimensional Elastic Light Scattering Fingerprints as Preneoplastic Markers in the Rat Model of Colon Carcinogenesis," Gastroenterology, 2004, vol. 126. pp. 1071-1081.

Wali, R.K. et al., "Increased Mucosal Blood Flow is an Early Marker of Colon Carcinogenesis," AGA Abstracts, Undated, p. A-4.

Wali, R.K. et al., "Increased Microvascular Blood Content in an Early Event in Colon Carcinogenesis," downloaded from gut.bmjjournals.com on Apr. 21, 2005, pp. 654-660.

Zonios, George et al., Diffuse Reflectance Spectroscopy of Human Adenomatous Colon Polyps in Vivo, Applied Optics, vol. 38, No. 31, Nov. 1, 1999, pp. 6628-6637.

Kim, Y. et al., "Low-coherent backscattering spectroscopy for tissue characterization," Applied Optics, vol. 44, No. 3, Jan. 20, 2005 (12 pages).

International Search Report in International Patent Application No. PCT/US10/20557, dated Mar. 8, 2010 (2 pages).

International Preliminary Report on Patentability dated Feb. 26, 2009 from PCT/US07/017894.

International Search Report and Written Opinion dated Mar. 19, 2008 from PCT/US07/017894.

Extended European Search Report in European Patent Application No. 07794779.4, dated Sep. 23, 2014.

Aug. 21, 2018 Office Action issued in European Patent Application No. 07794779.4.

\* cited by examiner

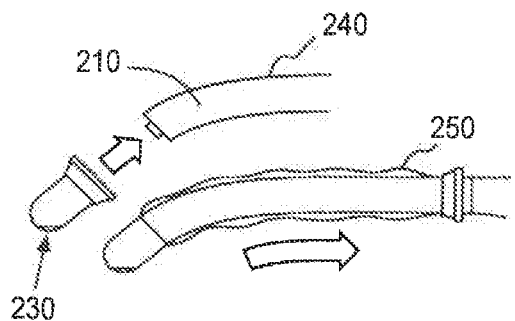
FIG. 7B
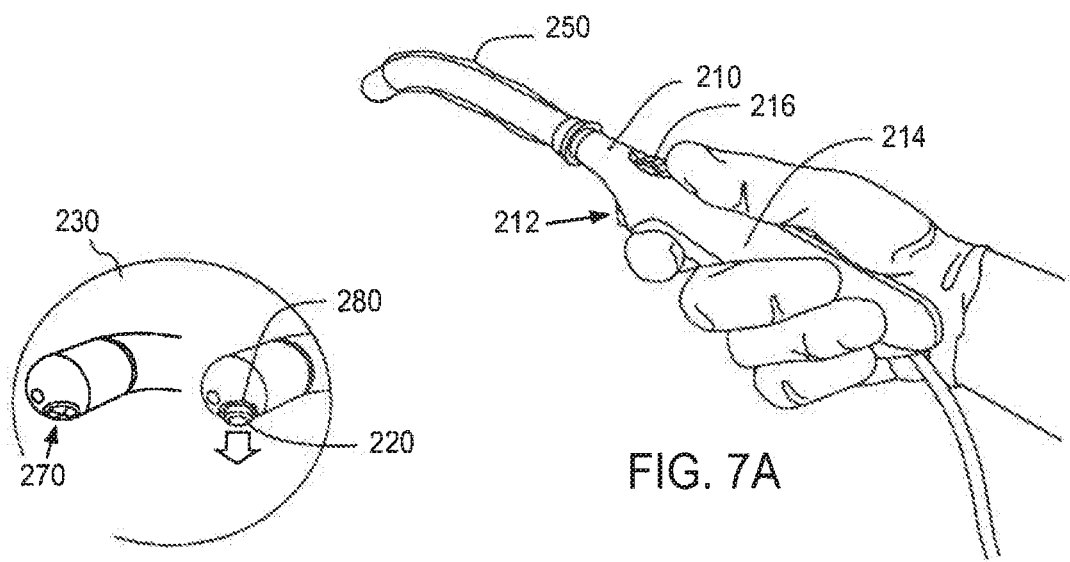
FIG. 7C
FIG. 7A
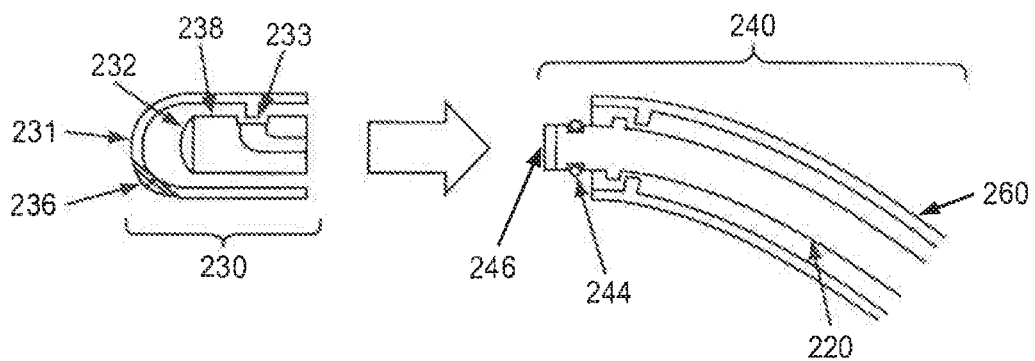
FIG. 8

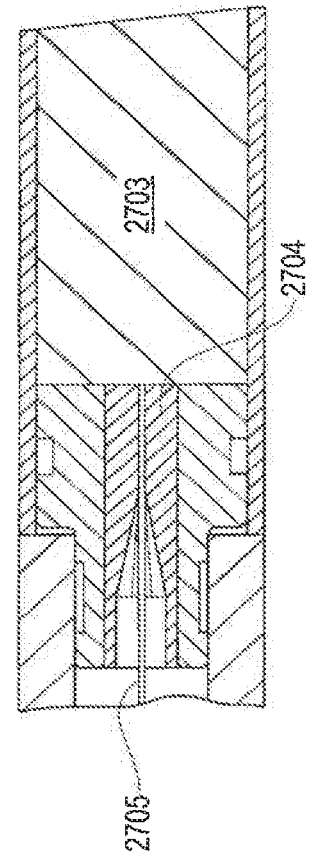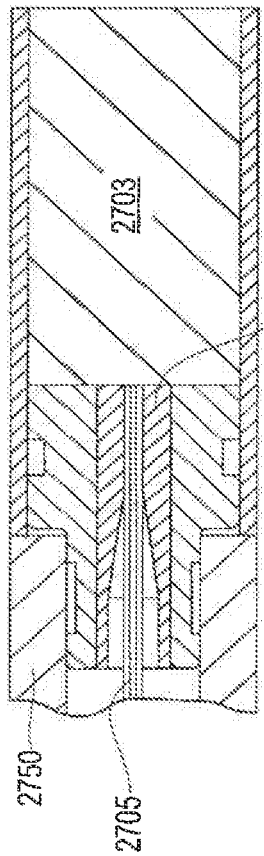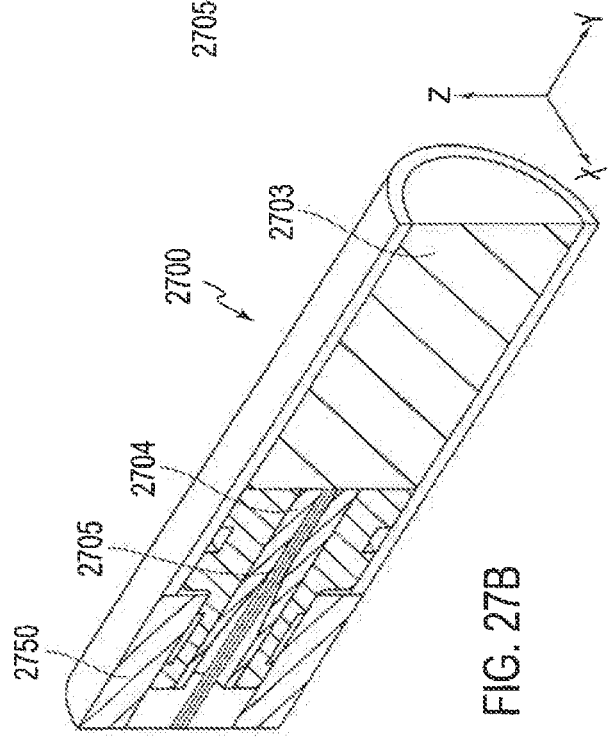
FIG. 27A
FIG. 27B
Z-Y SECTION
FIG. 27C
X-Y SECTION
FIG. 27D

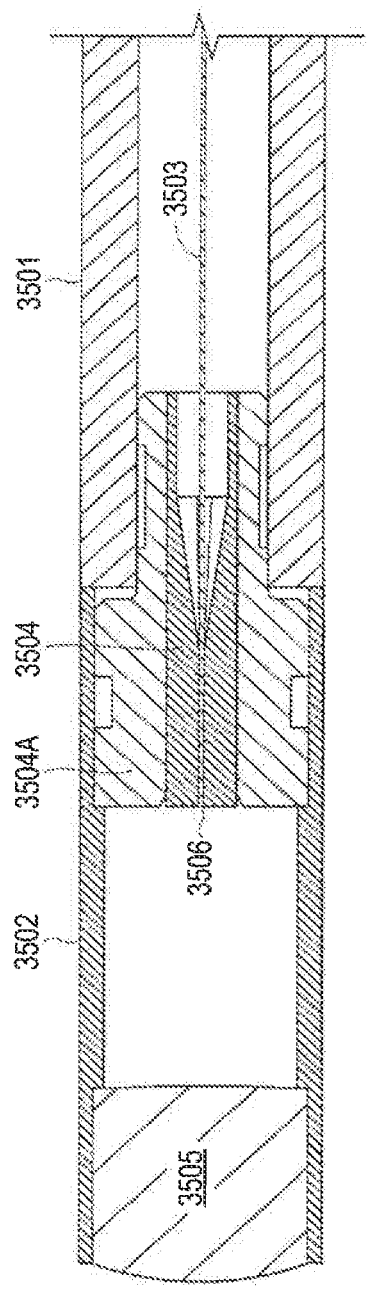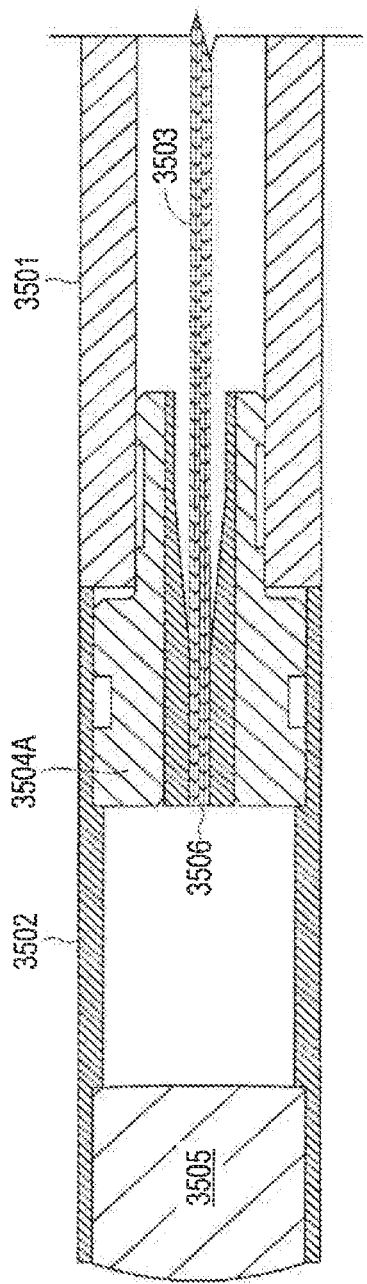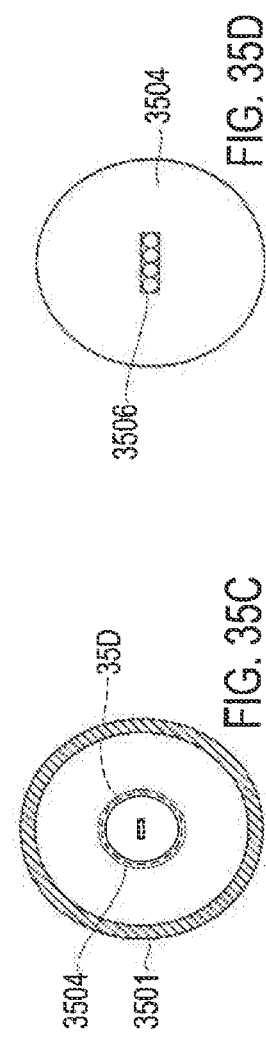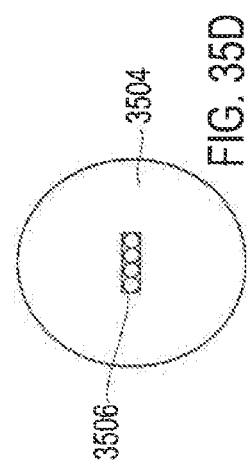

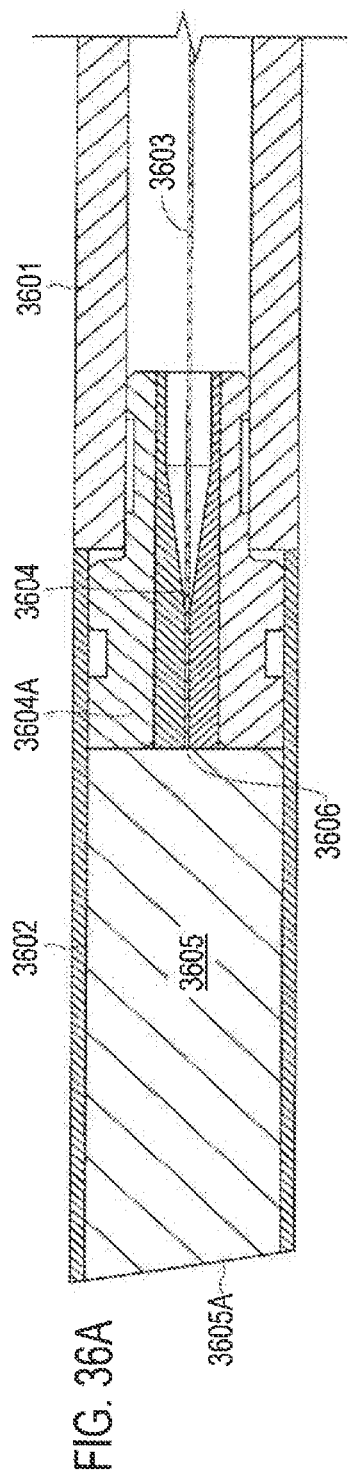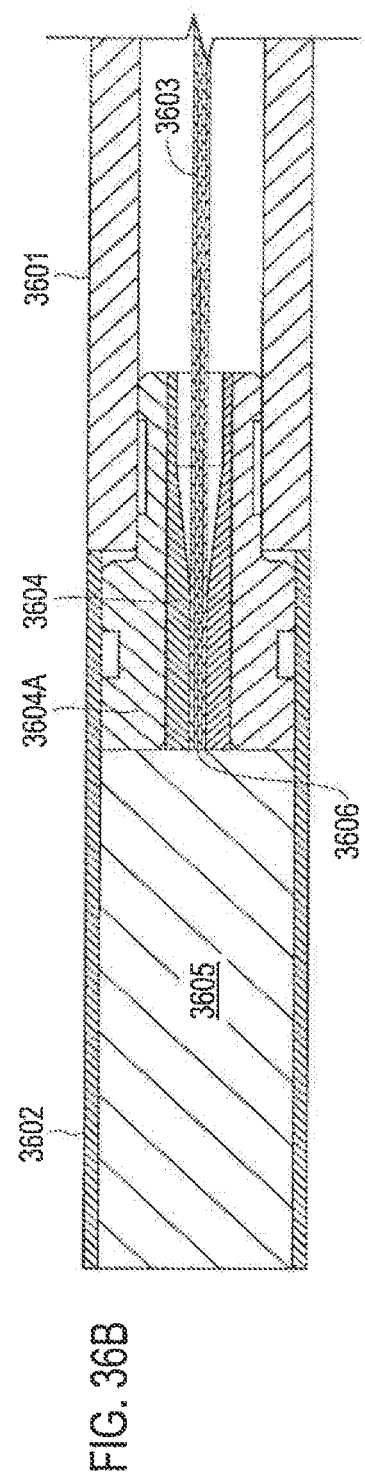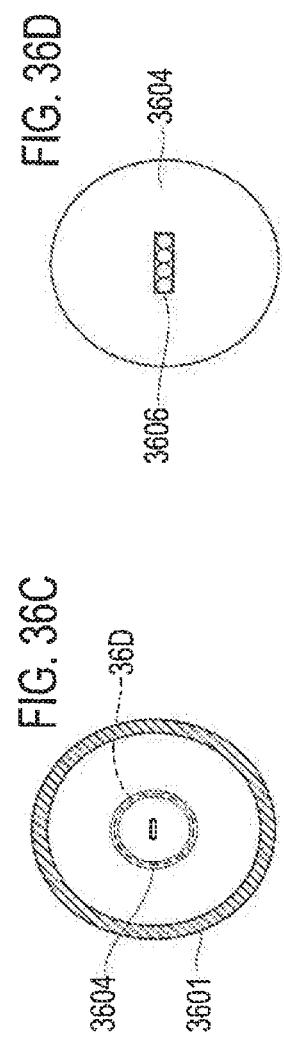

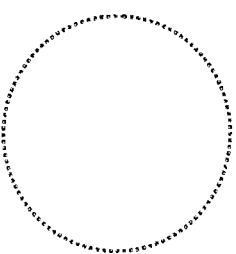
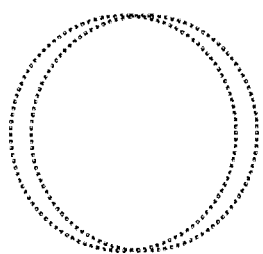
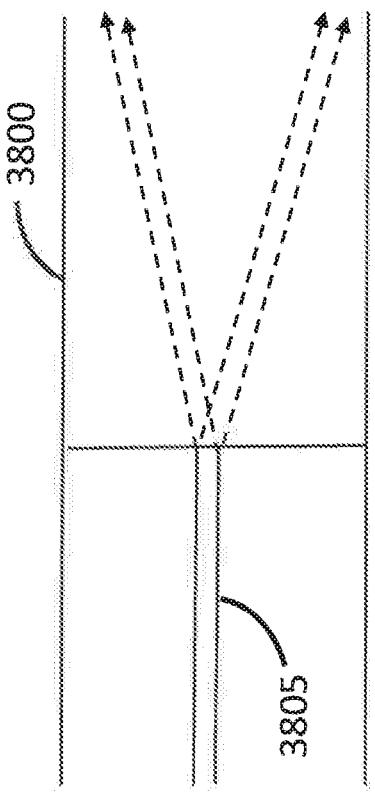
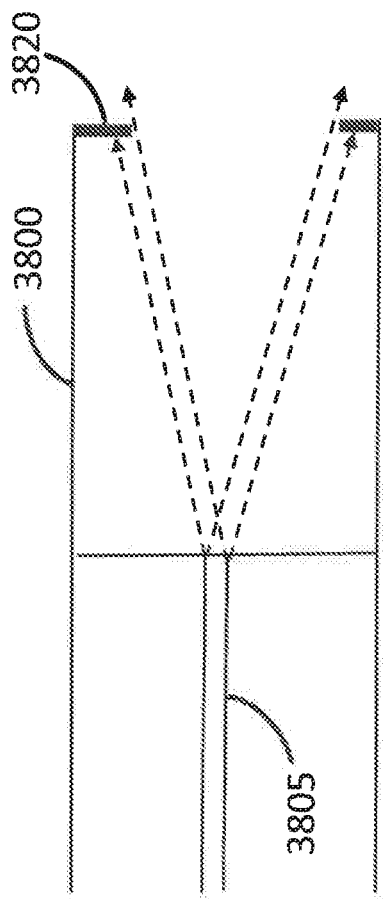

PROBE APPARATUS FOR MEASURING DEPTH-LIMITED PROPERTIES WITH LOW-COHERENCE ENHANCED BACKSCATTERING

RELATED APPLICATIONS

This application is a continuation-in-part of U.S. patent application Ser. No. 13/963,560, filed on Aug. 9, 2013, which is in turn a continuation-in-part of U.S. patent application Ser. No. 12/684,837 filed Jan. 8, 2010 and entitled "Probe Apparatus for Recognizing Abnormal Tissue," which claims priority to U.S. Provisional Patent Application No. 61/143,407 filed Jan. 8, 2009 and entitled "Probe Apparatus for Recognizing Abnormal Tissue," the entire contents of which are incorporated by reference.

This application is related to co-pending U.S. patent application Ser. No. 11/604,653 filed Nov. 27, 2006 and entitled "Method of Recognizing Abnormal Tissue Using the Detection of Early Increase in Microvascular Blood Content," the entire contents of which are incorporated by reference herein, which application claims priority to U.S. Provisional Patent Application Ser. No. 60/801,947 filed May 19, 2006 and entitled "Guide-To-Colonoscopy By Optical Detection Of Colonic Micro-Circulation And Applications Of Same," the entire contents of which are incorporated by reference.

This application is also related to co-pending U.S. patent application Ser. No. 11/604,659 filed Nov. 27, 2006 and entitled "Apparatus For Recognizing Abnormal Tissue Using The Detection Of Early Increase In Microvascular Blood Content," the entire contents of which are incorporated by reference.

This application is also related to co-pending U.S. patent application Ser. No. 11/261,452 filed Oct. 27, 2005 and entitled "Multi-Dimensional Elastic Light Scattering," the entire contents of which are incorporated by reference.

STATEMENT AS TO RIGHTS UNDER FEDERALLY-SPONSORED RESEARCH

This invention was made with government support under R01 CA128641, R01 EB003682, and R01 CA156186 awarded by National Institutes of Health and CBET-0937987 awarded by the National Science Foundation. The government has certain rights in the invention.

Some references, which may include patents, patent applications and various publications, are cited and discussed in the following description. The citation and/or discussion of such references is provided merely to clarify the following description, and is not an admission that any such reference is "prior art" to the subject matter disclosed herein. All references cited and discussed in this specification are incorporated herein by reference in their entireties and to the same extent as if each reference was individually incorporated by reference.

FIELD OF THE DISCLOSURE

The subject matter disclosed herein relates generally to light scattering and absorption, and in particular to probe apparatuses and component combinations thereof that are used to screen for possibly abnormal living tissue using Low-coherence Enhanced Backscattering (LEBS) spectroscopy.

BACKGROUND

Optical probes are known that detect optical signals. Simple optical probes will transmit broadband or a laser light to a target with one optical fiber, and receive the light such as light that is elastically scattered from a specimen, fluorescent light, Raman scattered light, etc., with another optical fiber. The received backscattered light can be channeled to a receiver, such as a CCD array, and the spectrum of the signal is recorded therein.

While such probes work sufficiently for their intended purposes, new observations in terms of the type of measurements that are required for diagnostic purposes have required further enhancements and improvements.

SUMMARY

Optical spectroscopy is a promising technique for the minimally invasive detection of cancers and precancers. The onset of precancer induces several structural changes in the mucosal morphology that result in changes in mass density distribution. According to the Gladstone-Dale equation, n (Refractive Index)=$n_{water}+\alpha\rho$, where p (g/ml) is the concentration of tissue solids (primarily macromolecules) and refractive index increment $\alpha$~0.17 to 0.2 ml/g. Thus, changes in the spatial distribution of mass density are directly related to changes in the distribution of refractive index. As a result, these changes in tissue morphology can be readily measured by analyzing the enhanced backscattering signal. The statistics (and their alteration in disease) of the spatial distribution of density and the corresponding refractive index can be parameterized by three quantities: (1) the variance of the spatial variations of refractive index $\Delta n^2$; (2) the correlation length of refractive index variation $l_c$; and (3) the shape of the correlation function m. These changes in physical properties lead to alterations in the macroscopic light scattering properties of tissue (e.g., reduced scattering coefficient $\mu_s^*$ and anisotropy coefficient g).

Most precancerous structural changes take place in the top mucosal layer, which causes changes in the light scattering properties of that layer. A modality which restricts the depth of interrogation photons to this layer maximizes the sensitivity of the measured optical properties to alterations in disease and provides an optimal diagnostic capability. Hence, the measurement of depth-limited optical properties serves as a tool to characterize the structure of any material, and can be diagnostically significant for tissue measurements.

The present disclosure relates generally to light scattering and absorption, and in particular to probe apparatuses and component combinations thereof that are used to recognize possibly abnormal living tissue. More particularly, this disclosure relates to probe apparatuses and components thereof that measure depth-limited optical properties in vivo using Low-coherence Enhanced Backscattering (LEBS) spectroscopy, and even more particularly, relates to a lens-free fiber optic LEBS probe capable of depth-limited in vivo measurements of the reduced scattering coefficient of tissue. LEBS spectroscopy is an angular resolved backscattering technique that is sensitive to sub-diffusion light transport length scales in which preserves information about scattering phase function, along with depth-limited interrogation (superficial depths).

Enhanced backscattering (EBS) is a result of the constructive interference between photons traveling time-reversed paths in a turbid medium. The EBS phenomenon manifests itself as an enhancement of scattered light intensity in the backward direction with respect to the incident light. The shape of an EBS peak as a function of angle is sensitive to $\mu_s^*$ and the shape of the phase function.

The majority of precancerous structural changes occur in the mucosal layer. These structural changes can be quantified by measuring changes in the depth-limited optical properties of this layer. LEBS is an attractive technique due to its ability to measure depth-resolved optical properties with sensitivity to sub-diffusion length scales. The inventors have shown in ex vivo studies that measurements of optical properties by LEBS in rectal mucosal biopsies were able to predict the risk of cancer being present elsewhere in the colon with 90% accuracy (area under ROC curve). This application discloses use of the LEBS technique with in vivo applications, and relates to the design and implementation of LEBS fiber optic probes, and in a preferred embodiment, a lens-free LEBS fiber optic probe. LEBS probe design was based on using the symmetric properties of the LEBS peak to obtain selective angular intensities from the LEBS peak to interpret and calculate depth-limited optical properties. Based on measurements obtained from phantoms and MC simulation, experimentally-observed LEBS parameters and optical properties closely matched the corresponding theoretically predicted LEBS parameters and optical properties. Additionally, MC simulations and two-layered phantom experiments verified the claim of depth selectivity (about the top 120 µm).

This application describes embodiments of fiber optic LEBS probes capable of providing in vivo depth-limited measurements of the optical and physiological properties. Generally, the principle of operation for such probes is the acquisition of the LEBS signal using optical fibers to collect a discrete number of backscattering angles. The embodiments described herein generally provide the ability to optimize the angular collection extent of the LEBS signal by optical fibers via minimization of the employed optical fiber core and subsequent outer diameter, and the resultant optical fiber center to center spacing.

In one aspect, the embodiments described herein are directed toward an LEBS probe apparatus, and in preferred embodiments a lens-free fiber optic LEBS probe apparatus, capable of providing depth-limited measurements of the reduced scattering coefficient in-vivo. The probe apparatus emits broadband light, typically obtained from a separate light source, onto microvasculature of tissue, such as a mucosal tissue layer disposed within a human body, and receives interacted light that is obtained from interaction of the broadband light with the microvasculature for transmission to a receiver.

In another aspect, the embodiments described herein are directed toward an LEBS probe apparatus, and in preferred embodiments a lens-free fiber optic LEBS probe apparatus, capable of providing depth-limited measurements of the reduced scattering coefficient in vivo. The probe apparatus emits broadband light, typically obtained from a separate light source, onto tissue disposed within a human body, such as a mucosal tissue layer disposed within a human body, and receives interacted light that is obtained from interaction of the broadband light with the microarchitecture tissue for transmission to a receiver.

In another aspect, embodiments described herein are directed toward an LEBS probe employing an optical lens in its distal tip, wherein the spacing between the optical fibers and optical lens varies the spatial coherence length of light, which in turn varies the penetration depth of probe. Thus, embodiments of the LEBS probe provide the ability to control the spatial coherence length of LEBS probe by varying: 1) the optical fiber core diameter, and 2) focal length of employed lens.

Further, embodiments of the LEBS probe employ a collinear and/or circular alignment of multiple fibers, wherein generally one fiber is used for illumination, and the remaining fibers are used for signal collection. In such embodiments, the LEBS signal forms at the plane of the illumination fiber, and is detected by the fiber array aligned collinearly or circularly with the illumination fiber.

In further embodiments, the optical lens of the LEBS probe may be housed inside a probe tip, separate from probe trunk containing optical fibers. When the tip and trunk are attached to form a single probe, the subsequent physical spacing between the optical lens and optical fiber end-face, or the end of the collinear fiber assembly, is used to set the spatial coherence length to the desired spatial coherence length.

In further embodiments, the LEBS probe features an optical spacer in the distal tip. The length of optical spacer varies the spatial coherence length of light, which in turn varies the penetration depth of probe.

In further embodiments, the optical spacer of the LEBS probe may be split into two parts, one part housed in a disposable probe tip assembly, and the other part house inside the probe trunk assembly. When the tip assembly and trunk assembly are attached to form a single probe, the two optical spacer parts form a single optical path, wherein the optical path length is predetermined to set the desired spatial coherence length and subsequent penetration depth.

Embodiments may feature a disposable, finger mounted LEBS probe.

Embodiments may also feature an LEBS probe that contains a disposable tip assembly with a retractable integral probe.

Embodiments of the LEBS probe are described which include various combinations of optical components to assist in the selection of a predetermined depth of interacted light, for a variety of different wavelength ranges of light, and for different applications.

BRIEF DESCRIPTION OF THE DRAWINGS

These and other aspects and features of the present disclosure will become apparent to those of ordinary skill in the art upon review of the following description of specific embodiments in conjunction with the accompanying figures, wherein:

FIGS. 7A, 7B and 7C show usage of an embodiment of an optical probe that contains a permanent housing and disposable tip with retractable integral optical fibers.

FIG. 8 illustrates a partial illustration of a particular embodiment of an optical probe that contains a permanent housing and a disposable tip assembly with a retractable integral optical fiber assembly.

FIGS. 27A-27D illustrate an embodiment of a lens-free LEBS fiber optic probe with a glass rod attached to a glass ferrule, containing four fibers arranged in a collinear array. FIG. 27B is a cross-section of the probe embodiment, and FIGS. 27C and 27D are the z-y and x-y cross sections, respectively, of the probe embodiment.

FIG. 32A shows a front-top-right side perspective view of the device. FIG. 32B shows a right side elevation view of the device.

FIGS. 35A-35D and 36A-36D illustrate preferred embodiments of a lens-based and a lens-free LEBS probe, respectively.

FIG. 38A illustrates an unmasked tip assembly with fibers projecting to target areas offset from each other. FIG. 38B illustrates the offset target areas.

FIG. 39A illustrates a masked tip assembly embodiment projecting to a target area. FIG. 39B illustrates the target area.

DETAILED DESCRIPTION OF THE PREFERRED EMBODIMENTS

Figure 1A:
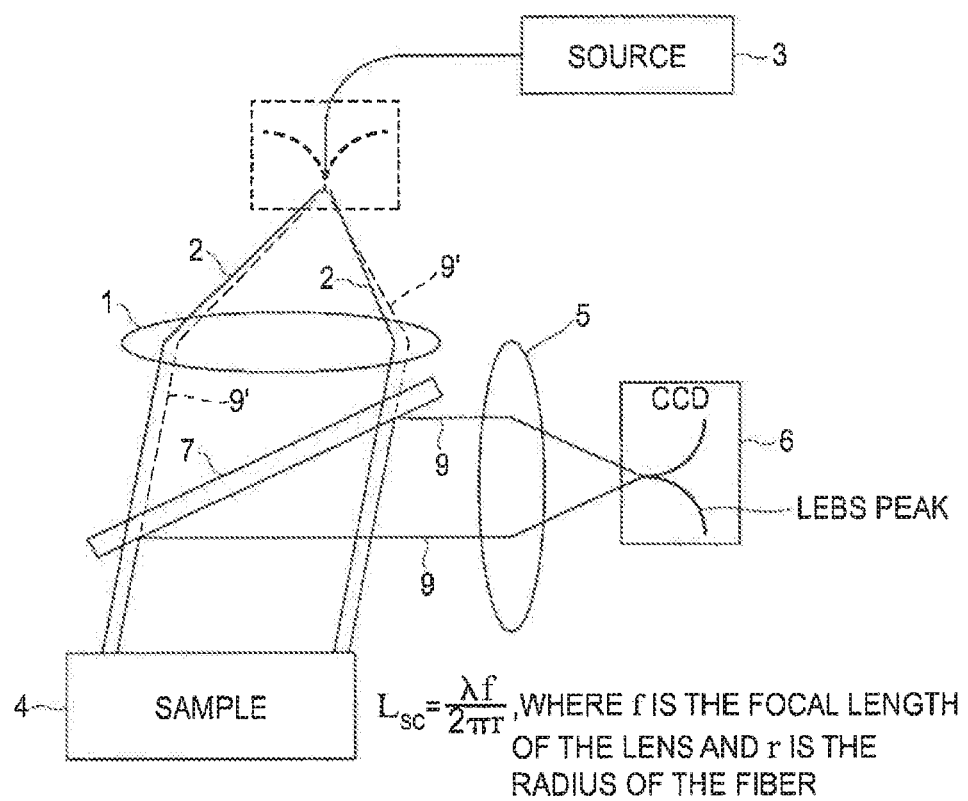
FIGS. 1A and 1B illustrate lens-based and lens-free techniques, respectively, for experimentally observing an LEBS peak.

The subject matter of the present disclosure is more particularly described in the following examples that are intended as illustrative only, since numerous modifications and variations therein will be apparent to those skilled in the art. Various embodiments are now described in detail. Referring to the drawings, like numbers indicate like components throughout the views. As used in the description herein, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present disclosure. Additionally, some terms used in this specification are more specifically defined below.

The terms used in this specification generally have their ordinary meanings in the art, within the context of the disclosure, and in the specific context where each term is used. Certain terms that are used to describe embodiments are discussed below, or elsewhere in the specification, to provide additional guidance to the practitioner regarding the description of embodiments, for convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, not is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein is illustrative only, and is in no way intended to limit the scope and meaning of the description of any embodiment, or of any exemplified term. Likewise, the principles and concepts in this disclosure are not limited to the embodiments described below.

Unless otherwise defined, all technical and scientific terms used herein have the same meaning as commonly understood by one of ordinary skill in the art to which this disclosure pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated. Enhanced backscattering (EBS) is a result of the constructive interference between photons traveling time-reversed paths in a turbid medium. The EBS phenomenon manifests itself as an enhancement of scattered light intensity in the backward direction with respect to the incident light. The shape of an EBS peak as a function of angle is sensitive to $\mu_s^*$ and the shape of the phase function.

The LEBS intensity peak defined by Equation (1) is the Fourier transform of the spatial backscattering impulse-response function (P(r)) multiplied by the spatial coherence function (C(r)):

$$I_{LEBS}(\theta)=FT[P(r)\cdot C(r)] \quad (1)$$

The C(r) function (and $L_{SC}$) can be controlled experimentally, whereas $I_{LEBS}(\theta)$ is recorded by means of a lens projecting the angular distribution of reflected light onto a focal plane as shown in FIG. 1A. The P(r) function at sub-diffusion length scales and the optical and physical properties of tissue can therefore be calculated from Equation (1). The light scattering optical properties of tissue ($\mu_s^*$, g & $D_f$ (fractal dimension)) can be measured by fitting the measured LEBS peak to, for example, properties obtained numerically by Monte Carlo simulations or using a look-up Table.

Using an LEBS bench top system, the inventors have demonstrated that low spatial coherence illumination (coherence length $L_{SC} \ll l_s^*$, $l_s^*=1/\mu_s^*$, light transport mean free path ~1 mm) facilitates the detection and quantification of the EBS effect in tissue. Depth selectivity is achieved by selecting $L_{SC}$, which acts as a spatial filter limiting the radial displacement of photons that interfere to form the LEBS peak (a smaller $L_{SC}$ rejects the signal from deeper tissue, resulting in a shorter average penetration depth). Ex vivo measurement of optical properties in rectal mucosal biopsies using the LEBS bench top system predicted the risk of future neoplasia elsewhere in the colon with about 90% accuracy (area under ROC curve). However, the bench top system is better suited for ex vivo measurements, due to its large size (FIG. 1). Thus, a need exists for an LEBS probe suitable for in vivo use. In setup shown in FIG. 1A, the first lens 1 collimates the beam 2 from a broadband light source 3 onto the sample 4. In lens-based observation, the beam of light from a broadband light source is collimated using a lens 1 and relayed to the sample 4; the backscattered light 9 is then collimated by a lens 5 onto a detector 6. When the illumination is collimated, the source 3 can be described as being located infinitely far from the sample 4, and therefore the peak is localized at infinity. The backscattered signal can be collected by another lens 5 and focused onto an imaging camera or a charge-coupled device 6 (CCD) by using an optical component to collect scattered light back into the CCD or camera, such as a beam splitter 7. Alternatively, as depicted by the broken lines 9' in FIG. 1A, the LEBS peak can also be observed in the retro-reflection direction in the plane of the light source 3 in the absence of beam splitter 7. Both setups yield identical information, however, and differ only in the number of required optical components. For example, in a setup without a beam splitter 7, lens 5 is removed, thereby resulting in a more compact setup. While the more compact setup is preferred for fiber optic probe applications, either setup is suitable for use with a fiber optic probe.

Figure 1B:
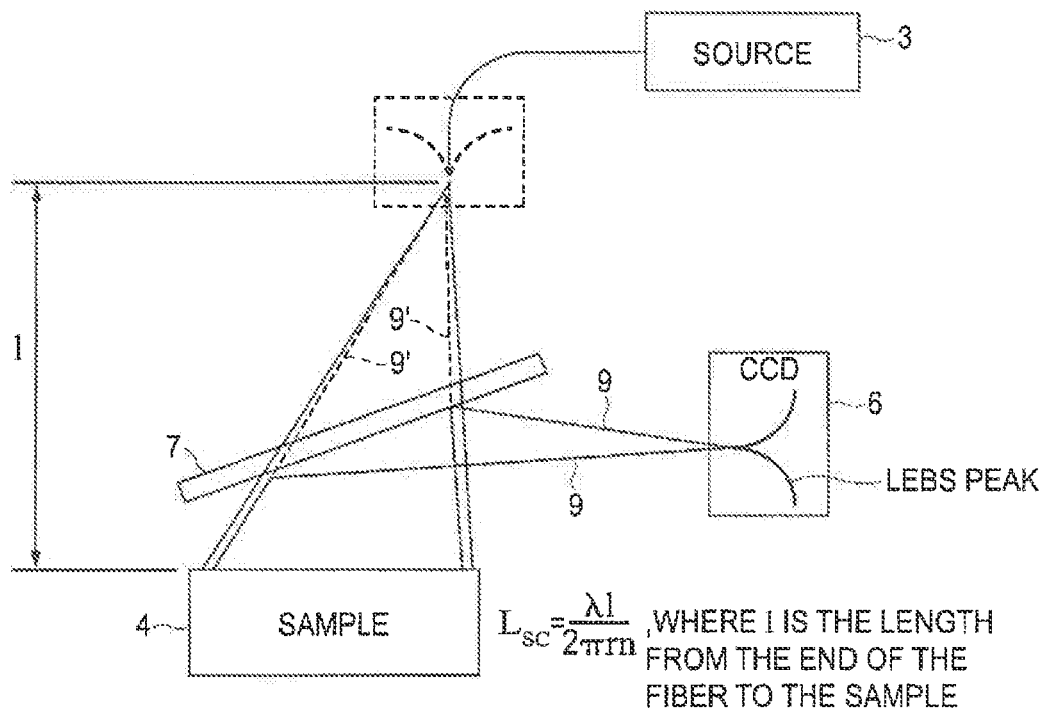

Another alternative is a lens-free assembly, as depicted in FIG. 1B. The lens-free assembly works on the principle of phase conjugation, in which the light source at a finite distance from the medium produces the peak at a point conjugate to the source. In the lens-free setup, a diverging illumination beam 8 removes the need for lenses. The diverging beam 8 illuminates the sample 4 with broadband light from light source 3, and the backscattered light 9 forms a peak at the phase conjugate points, i.e., the point in space conjugate to the source. Like the lens-based LEBS setup, the lens-free configuration can be used with or without beam splitter 7, such that the LEBS peak can also be observed in the retro-reflection direction in the plane of the light source 3 as represented by broken lines 9'. Also, the lens-free configuration captures the same LEBS peak as the lens-based setup. However, eliminating the need for lenses and a beam splitter is advantageous for building compact and low-cost LEBS fiber optic probes for in vivo applications.

The present disclosure, in some aspects, relates to probe apparatuses, and components therefore, for optically screening a target for abnormal tissue (e.g., cancer, precancer, tumors, or lesions). Various targets and corresponding optical probe types are disclosed, as well as various different probe housing designs are disclosed, and combination of them can be used interchangeably. Certain optical probe designs are useful for detecting what is referred to as "Early Increase in microvascular Blood Supply" (EIBS) that exists in tissues that are close to, but are not themselves, the lesion or tumor. Certain optical probe designs are suitable for LEBS spectroscopy, e.g., detecting enhanced backscattered light that results from the interaction of low-coherent light with abnormal scattering structures in the microarchitecture of the tissue that exist in tissues that are close to, but are not themselves, the lesion or tumor. The probes described herein, while normally made for usage with one of these techniques, have aspects that are common between them. Thus, although certain features may be described in connection with, for example, an EIBS probe, such features may be used with an LEBS probe.

One difference between a probe that detects EIBS and an LEBS probe that detects tissue microarchitecture is that with an probe that detects EIBS, data from a plurality of depths can be obtained in one measurement by looking at co-pol and cross-pol and co-pol minus cross-pol received signals, whereas for an LEBS probe, only one depth is obtained for a specific configuration.

A particular application described herein is for detection of such lesions in colonic mucosa in early colorectal cancer ("CRC"), but other applications such as pancreatic cancer screening are described as well.

The target is a sample related to a living subject, particularly a human being. The sample is a part of the living subject, such that the sample is a biological sample, wherein the biological sample may have tissue developing a cancerous disease.

The neoplastic disease is a process that leads to a tumor or lesion, wherein the tumor or lesion is an abnormal living tissue (either premalignant or cancerous), which for the probes described herein is typically a colon cancer, an adenomatous polyp of the colon, or other cancers.

The measuring step is performed in vivo using the probes described herein and may further comprise the step of acquiring an image of the target. The image, obtained at the time of detection, can be used to later analyze the extent of the tumor, as well as its location.

Generally, in the embodiments described herein, the probe projects a beam of light to a target that has tissues and/or blood circulation associated therewith, depending upon the target type. Light scattered from the target is then measured, and target information is obtained from the measured scattered light. The obtained target information can be information for the targets as described in the patent applications incorporated by reference above, as well as the data related to blood vessel size and oxygenated hemoglobin as described in U.S. patent application Ser. No. 12/350,955 filed Jan. 8, 2009 entitled "Method Of Screening For Cancer Using Parameters Obtained By The Detection Of Early Increase In Microvascular Blood Content," the entire contents of which are incorporated by reference.

The probe projects a beam of light obtained from a light source that may be separate from the probe, and that may comprise an incoherent light source (such as a xenon lamp, light emitting diode, etc.).

In the embodiments described herein, there is at least one first type fiber comprises an illumination fiber, wherein the illumination fiber is optically coupled to the light source.

There is also at least one second type fiber formed with one or more collection fibers, wherein the one or more collection fibers are optically coupled to a detector, such as an imaging spectrograph and a CCD at the distal end portion, which imaging spectrograph is used to obtain an image of the target and obtain detected data therefrom.

The following description further details the preferred embodiments. Without intent to limit the scope of the disclosure, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

The optical probes described herein can be used in vivo to take optical measurements of tissue to screen for abnormal tissue, such as, for example, tissue just inside the rectum to assess a patient's risk of colon cancer. When used for assessing risk of colon cancer, the rectally inserted probe for analysis of rectal mucosa provides a means of assessing a patient's risk of developing colon cancer without the need for colonoscopy or colon purging. Although portions of the following description relates to embodiments for assessing risk of colon cancer, the optical probes described may be used to screen for a wide variety of abnormal tissue, such as pancreatic, lung, esophageal, and cervical cancers.

In order to facilitate the acquisition of such a measurement for assessing risk of colon cancer, the probe is typically introduced into a patient's colorectal vault via an insertion device, such as a colonoscope, an upper GI therapeutic scope, a disposable, finger mounted device, or an optical probe that contains a permanent housing and disposable tip with retractable integral optical fibers.

For clinical evaluation of a colon, the probe is inserted into the rectum to establish contact with the colorectal mucosal wall, perform optical measurements as needed, and is then removed. The probes described further herein may include an insertion device for guiding the probe on a pathway through the rectum to reach the colorectal mucosal wall, while shielding the probe tip from possible blockage caused by, for example, loose stool that the probe may encounter. While contacting the colorectal mucosal wall, the insertion device may allow the optical portion of probe to extend some distance out of the tip of the insertion device and perform optical measurements as needed.

The optical probes with insertion devices described herein may contain components that are partially or entirely disposable, since for health reasons certain components are preferably not used with multiple patients.

Figure 2:
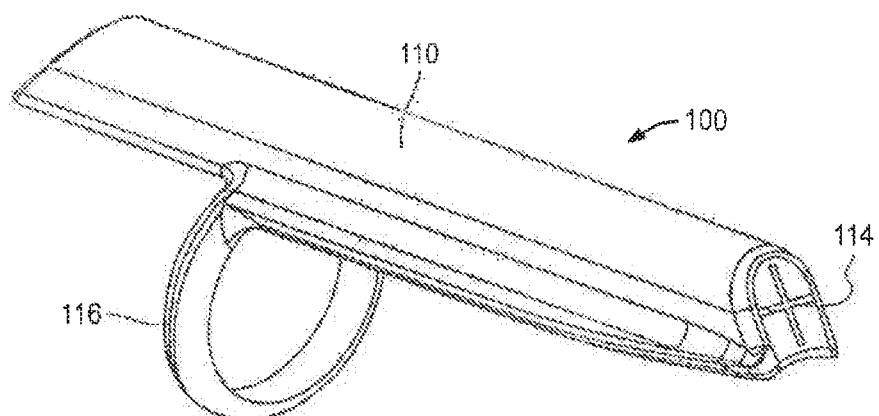
FIGS. 2 and 3 illustrate a housing of a disposable, finger mounted optical probe according to one embodiment.
Figure 3:
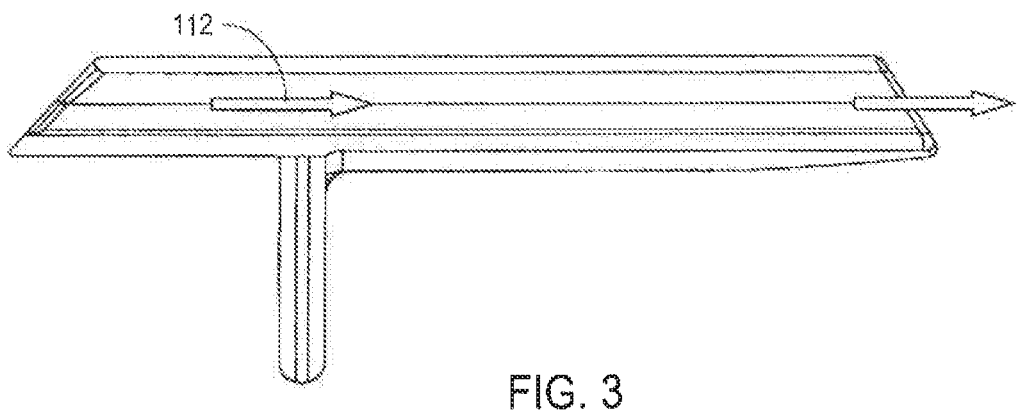
Figure 4:
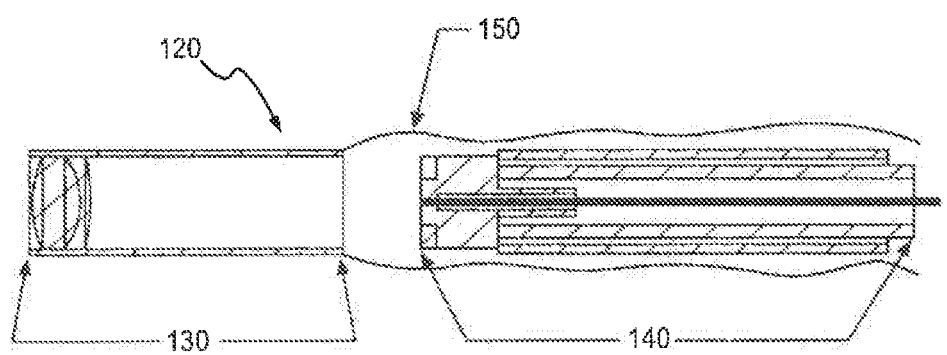
FIG. 4 illustrates a disposable tip and re-usable trunk usable in one embodiment of the disposable, finger mounted optical probe.

One example of a disposable component is a finger mounted optical probe configured to connect to optical fibers in a reusable trunk assembly. FIGS. 2-4 illustrate a housing 110 of a disposable, finger mounted optical probe 100 according to one embodiment, which is a semi-flexible component that includes a finger loop 116 worn over the physicians finger. As shown in FIG. 4, incorporated within the housing 110 is a complete optical probe 120, including at least a portion of re-usable trunk assembly 140, and a disposable tip 130, described further herein, which are connected together by some type of engagement mechanism, such as threads on both the tip assembly 130 and the trunk assembly 140. FIG. 4 shows only a portion of the trunk assembly 140. In practice, the trunk assembly 140 may extend several feet for eventual connection to other components, such as a light source and a spectrophotometer. This finger mounted optical probe 100 is inserted into the patient's rectum while mounted on the finger of the physician, allowing for passage of the optical probe 120 to the mucosal wall for measurement acquisition while shielding from potential loose stool both the optical probe, and particularly the optical components of the optical probe 120 that are disposed within the disposable tip 130.

The housing 110 of the disposable, finger mounted optical probe 100 is sufficiently lubricious to provide for easy passage of optical fibers through internal lumen 112, and on its outer surface for non-lubricated device insertion into a patient's rectum. The housing may be made of liquid injection molded silicone rubber or similar material. Further, a parylene-N coating may be added to some or all surfaces of the housing 110 to increase overall lubricity for ease of feeding of probe through inner lumen, and insertion into the patient.

The outer front surface of the housing 110 preferably includes a perforated membrane 114 that shields the probe tips from loose stool that may be encountered within the patient, through which the probe tip can pass through just prior to acquisition of optical measurement on the mucosal wall, as described herein, though such a perforated membrane 114 is not necessarily needed.

Further, the disposable, finger mounted optical probe 100 will preferably either have: 1) a pre-formed geometry/curvature such that it can be guided to the proper location in the colorectal mucosal anatomy, 2) sufficient flexibility such that the physician can bend and/or manipulate it to the same area for optical measurement, or 3) some combination of both aforementioned attributes. If preformed, the probe 100 preferably has flexibility such that it could be inserted in a straight fashion, and shape memory such that it would retake its original shape once fully inserted into patient's colorectal vault.

The probe 100 as illustrated in FIGS. 2-4 allows for pass through of a fully assembled optical probe. This embodiment generally requires the disposable tip 130 to be attached to the reusable trunk assembly 140 prior to insertion. The disposable tip 130 is clean or sterile when initially used prior to insertion, and may also include a hygienic sheath 150 that acts as a hygienic shield to cover a portion of the reusable trunk assembly 140, which need not be sterile or sterilized when used. The hygienic sheath 150 may be made of a sterile thin polyethylene film or similar material.

Figure 5A:
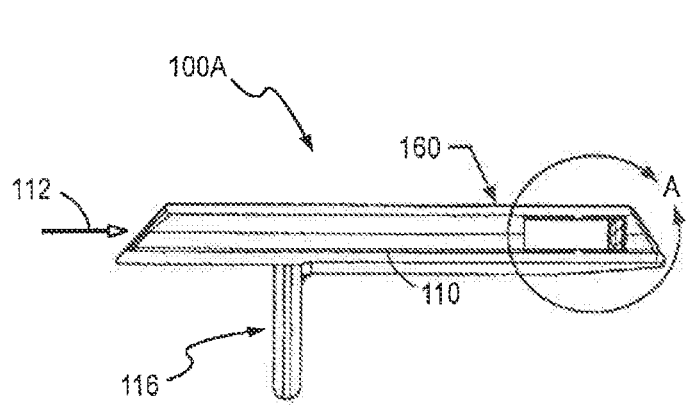
FIGS. 5A and 5B illustrate another embodiment of the disposable, finger mounted optical probe containing a pre-loaded optical assembly.
Figure 5B:
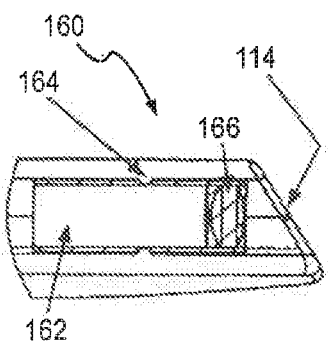

FIGS. 5A-5B illustrate another embodiment of the disposable, finger mounted optical probe 100A containing a pre-loaded optical assembly. In this embodiment, the housing 110 and the lumen 112 therein provides for pre-loading of an optical assembly 160, such that the re-usable trunk (as described with reference to FIG. 4) will connect to the optical assembly 160 (essentially the same as the disposable tip 130) within the lumen 112, and the entire assembly, once connected, can then continue to be positioned by moving through the lumen 112, and eventually out through any perforated membrane 114. As shown in FIG. 5B, the optical assembly, in one embodiment, may include a lens mount 162, a rolling diaphragm 164 that provides fixing of the optical assembly and a hygienic seal. This hygienic seal can be simply a narrowing of the lumen such that the lens mount 162 fits tightly around the optical assembly to prevent fluid from flowing backward but is not so tight as to prevent the optical assembly from sliding forward and back, and a lens 166, though other components, such as polarizers and spacers, can also be used within optical assembly 160.

In the embodiment of FIG. 5A and FIG. 5B, the hygienic sheath is preferably attached to the disposable housing 110 at the entry end 118 of the housing. Though the sheath is not shown in FIG. 5A or FIG. 5B, it could also be attached within the lumen 112 and be part of the optical assembly 160 to address the possibility of cross-contamination. This sheath would extend back to cover all non-disposable surfaces of the probe assembly which may be manipulated by the physician. The finger-mounted insertion device 100A is preferably entirely disposable, and intended for single-use. An advancement assist ring 116 may be permanently attached to the optical probe to facilitate single handed probe insertion.

Figure 11:
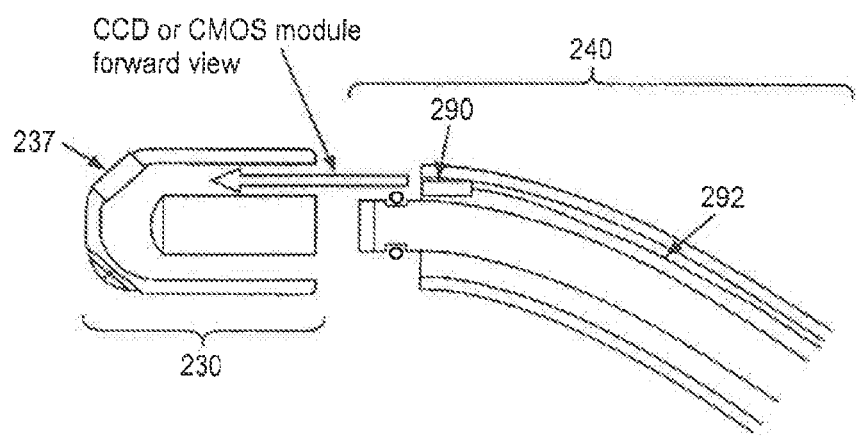
FIG. 11 illustrates a partial illustration of a further particular embodiment of an optical probe that contains a permanent housing and disposable tip assembly with a retractable integral optical fiber assembly and an integral CCD module.

Measurement acquisition may be initiated by a foot pedal connected to an instrumentation unit, a button built into the reusable portion of the probe assembly, or some other mechanism. If blind measurement acquisition and/or insertion is not deemed acceptable, a forward viewing CCD or CMOS camera module may be designed into the device, with camera residing in the reusable probe trunk, and window built into the disposable insertion device, as shown in FIG. 11.

Figure 6A:
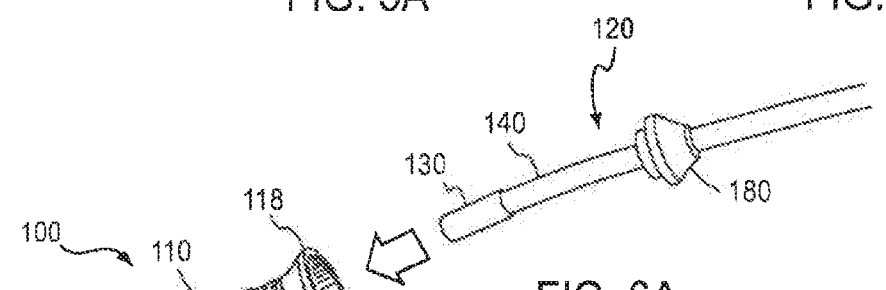
FIGS. 6A, 6B and 6C are illustrations of the method of use of the disposable, finger mounted optical probe.
Figures 6B, 6C:
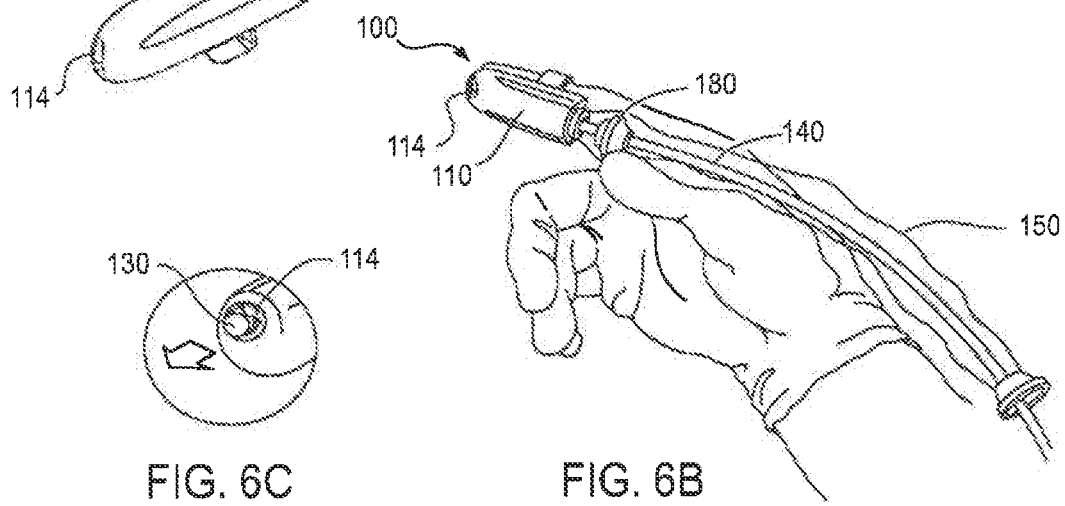

FIGS. 6A-6C are illustrations of the method of use of the disposable, finger mounted optical probe 100. In use, the probe assembly 120, formed of the re-usable trunk 140 and the disposable tip 130, is inserted into the housing 110 as shown, and an advancement assist ring 180, permanently attached to the re-usable trunk 140, will attach to the end 118 of the housing 110. As shown in FIG. 6B, the sheath 150 is pulled back so that it extends sufficiently below the sterile gloved hand of the physician to provide a sterile environment for the patient. As shown in FIG. 6C, the disposable tip 130 of the probe assembly 120 is pushed through the perforated membrane 114 at the time the measurement is taken.

FIGS. 7A, 7B and 7C show usage of an embodiment of an optical probe 200 that contains a permanent housing 210 and a disposable tip assembly 220 with retractable integral optical fiber assembly 220 (essentially the same as the optical assembly 120 that is formed of the disposable tip 130 and the re-usable trunk 140 as described in the FIG. 4 embodiment above), as well as an overall view of this embodiment. In all of the embodiments there exist the permanent housing 210, which preferably includes thereon a trigger activation button 212, a grip 214 for holding in the physician hand, and a roller wheel 216 or similar element integrated into the housing 210 to facilitate single-handed probe advancement, as shown in FIGS. 7A and 7B show at a high level both the connection of the disposable tip assembly 230 to the re-usable trunk assembly 240, as well as the unwrapping of the protective sheath 250 over the exterior of the housing 210. It is noted that in FIG. 7A the sheath 250 is only shown unrolled on the insertion portion 260, but preferably the sheath 250 will extend below the entire housing 210. FIG. 7C provides close up views of the disposable tip assembly 230, and shows both a CCD forward viewing window 270 for a CCD array disposed therebehind (not shown here, though components illustrated in FIG. 11 can work herein), as well as the perforated membrane 280 through which the disposable tip 220 assembly will be moved when the measurement is taken. In use, the insertion portion 260 is inserted into the patient's rectum, with the grip 214 of the housing 210 held by the physician, allowing for internal optical assembly to be positioned on the mucosal wall while shielded from potential loose stool. This allows for advancement of the internal optical probe assembly, including the lens as described hereinafter, out of the protective cap associated with the disposable tip assembly 220, and onto the patient's colo-mucosal wall for measurement acquisition.

In a preferred implementation, the housing 210 a two-piece, rigid injection molded handle comprised of ABS (Acrylonitrile butadiene styrene) or similar material. Further, an overmolded soft-touch material such as Pebax or Hytrel may comprise the insertion portion 260. The disposable tip assembly 230 in this configuration may be comprised of a similar soft-touch material overmolded soft-touch material such as Pebax or Hytrel. The hygienic sheath 250 attached to the lens mount 238 within disposable tip assembly 230 may be made of a thin polyethylene film or similar material.

It is noted that it may be that a sheath 250 isn't used, and the insertion portion 260 is sterilized after each use. In such a use, the insertion portion 260 is preferably lubricious enough on its outer surfaces for non-lubricated device insertion into a patient's rectum.

Further, this probe 200 also preferably has 1) a pre-formed geometry/curvature such that it locates the internal optical assembly, and particularly the optical tip, onto proper location in the colo-rectal mucosal anatomy, and 2) sufficient flexibility such that the physician could bend and/or manipulate the device to the same area for optical measurement. The probe 200 is sufficiently flexible such that it can be inserted in a straight fashion, and has shape memory such that it retakes its original shape once fully inserted into patient's colorectal vault.

FIG. 8 illustrates a partial illustration of a particular embodiment of an optical probe 200A, with only the optical components shown, not the sheath 250 and lower part of the housing 210. The shown semi-flexible insertion portion 260 contains therein the retractable integral optical fiber assembly 220, formed of the disposable tip assembly 230 and the trunk assembly 240. As shown the trunk assembly 240 will contain an outer sheath 248, which preferably includes at the distal end a protrusion ring 242, which abuts a similar protrusion ring 262 associated with the insertion portion of the housing 210. Also associated with the re-usable trunk assembly 240 is a springing engaging mechanism 244 for the optical components of the disposable tip assembly 230 to connect in an aligned manner, as well as, in certain configurations, other optical components 246, such as a polarizer or protective cover. Other engagement mechanism, such as threads on both the tip assembly 230 and the trunk assembly 240 can be used.

Figure 10:
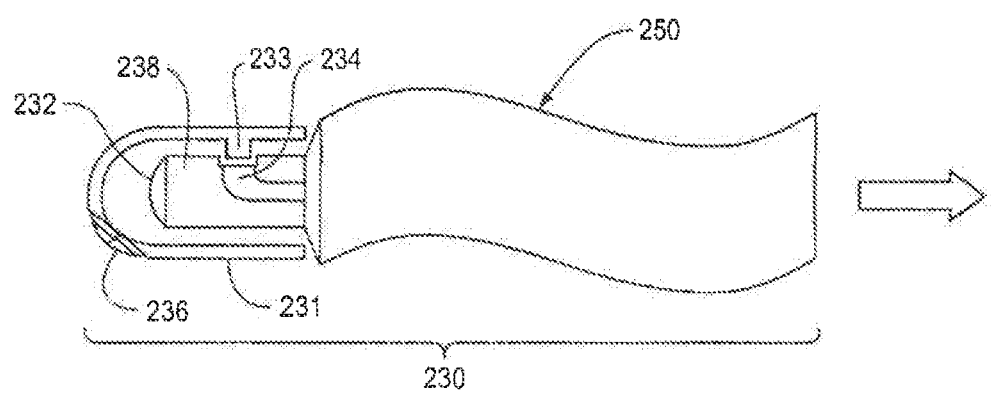
FIG. 10 illustrates a particular embodiment of a disposable tip that includes a protective sheath that is used with the optical probe that contains a permanent housing and disposable tip assembly with a retractable integral optical fiber assembly.

The disposable tip assembly 230 contains a protective cap 231 that has an alignment element 233 and perforated membrane 236, described further herein, that maintains the lens mount 238 in place prior to connection to the optical fiber trunk assembly 240. As shown in FIG. 10, the disposable tip assembly also preferably has attached thereto the sheath 250

The lens mount 238 will contain a lens 232, such as a GRIN lens, a ball lens, an achromatic doublet lens, etc., can be used, disposed therein or as part of a one-piece assembly, as well as an alignment member 234 that engages with the alignment element 233. The alignment member 234 in one embodiment is a channel into which a protrusion that is the alignment element 233 fits. Once the disposable tip assembly 230, and specifically the lens mount 238, is connected to the trunk assembly 240, and the engaging mechanism 244, the entire optical assembly 220 is moved through the rectum to the measurement point. At that time, the optical fiber assembly 220 can be slightly rotated and moved forward, so that the lens mount 238, via the alignment member 234, is guided by the alignment element 233, so that the lens 232 can protrude through the perforated membrane 236.

Figure 9:
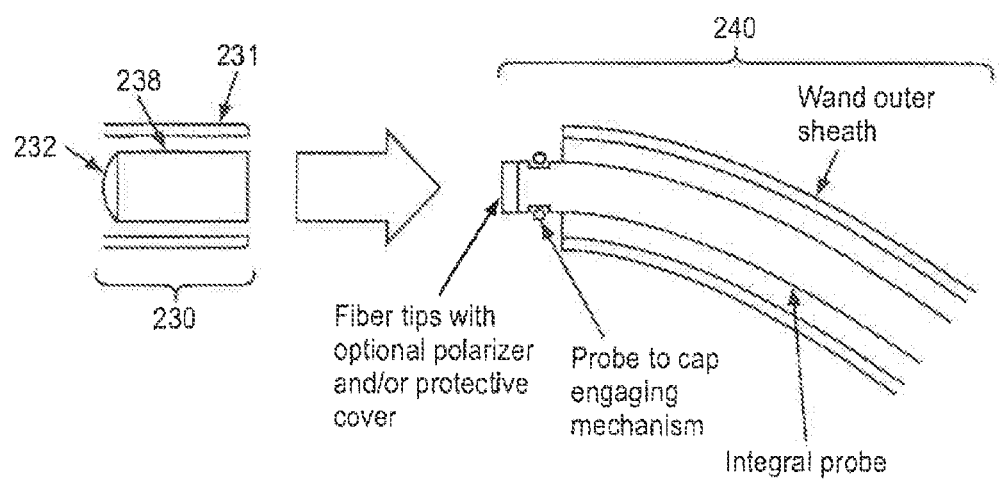
FIG. 9 illustrates a partial illustration of another particular embodiment of an optical probe that contains a permanent housing and disposable tip assembly with a retractable integral optical fiber assembly.

FIG. 9 illustrates a partial illustration of a particular embodiment of an optical probe 200B, with only the optical components shown, not the sheath 250 and lower part of the housing 210. In this embodiment, as shown the disposable tip assembly 230 does not contain a front face to the protective cover 231 or a perforated member, and as such the lens 232, mounted in the lens mount 238, is exposed. Otherwise, the elements shown in FIG. 9 are the same as those described previously with respect to FIG. 7. Since the lens 232 is pre-exposed, the probe 200B does not required advancement of retractable integral optical fiber assembly 220 to break through any protective cap membrane. Thus, once inserted and put into contact with the patient's colo-mucosal wall, the probe 200B is immediately ready for measurement acquisition.

If blind insertion is not deemed acceptable, a forward viewing CCD camera may be designed into the device, with camera residing in the tip of reusable portion of the wand, and window built into the disposable wand tip, as shown in FIG. 11. As shown, the disposable tip assembly 230 is modified by including the glass viewing cover 237 as part of the protective cap 231, and the probe 200 further includes a CCD or CMOS module, as will as an image return wiring 292 as needed. Depending on the configuration, the CCD or CMOS module may include battery power, may be powered via wires for the power, and/or the power and/or image signals may be transmitted wirelessly using various conventional data and short range power transmission schemes.

Different penetration depths are implemented with these probes in a variety of ways. Different fibers and/or disposable tips can be used (in some instances with different probes, in other instances all within the same probe) in order to achieve the desired results. For probes that detect EIBS in particular, the choice of the spacing between the fiber termination and lens (e.g. nominally 1 focal length but could be more or less) and selection of the lens type and focal length adjustment depth can be used to achieve different penetration depth. For LEBS probes that detect tissue microarchitecture, the selection of the lens and the distance from the termination of the fibers to the lens or the length of the glass spacer determine the special coherence length of light, which will vary the penetration depth.

In use, depending upon the target and the application, each probe may take multiple measurements, and the detected data from each measurement stored for subsequent usage. Typically a number of different measurement locations, such as 3-6, but not typically greater than 10 will be made. Depending on the probe or the manner in which the probe is used, various different penetration depths may then be sensed at each measurement location.

Figure 12:
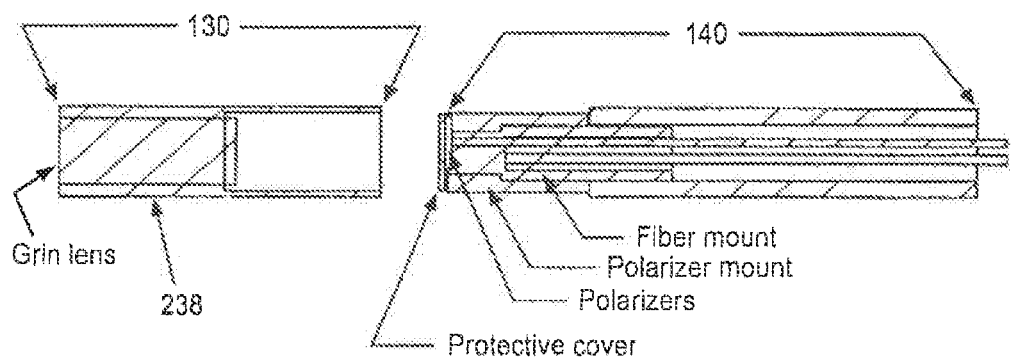
FIG. 12 illustrates a particular optical probe assembly configuration used for EMS.
Figure 13:
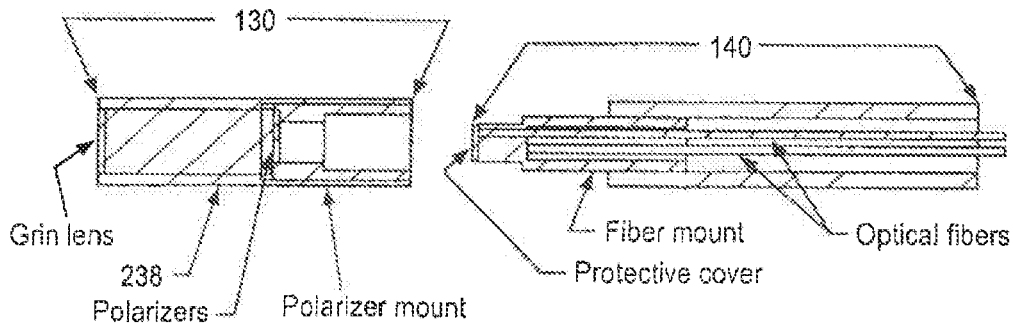
FIG. 13 illustrates another particular optical probe assembly configuration used for EMS.
Figure 14:
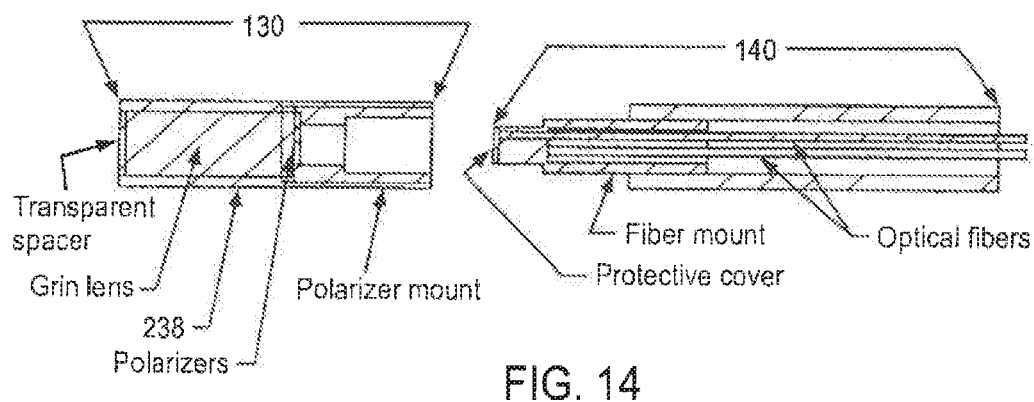
FIG. 14 illustrates a further particular optical probe assembly configuration used for EMS.

FIG. 12 illustrates a particular optical probe assembly configuration used for EIBS. FIG. 13 illustrates another particular optical probe assembly configuration used for EMS. It is noted that the lens mount and polarizer mount may be combined to form a single component. FIG. 14 illustrates a further particular optical probe assembly configuration used for EIBS. It is noted that the lens mount and polarizer mount may be combined to form a single component. In each of FIGS. 12, 13 and 14, the components are identified, and they together show that various combinations of components can be used: certain embodiments may or may not have polarizers, spacers and different numbers of optical fibers can also be used. In this regard, reference is made to the previously filed U.S. patent application Ser. No. 11/604,659 filed Nov. 27, 2006 and entitled "Apparatus For Recognizing Abnormal Tissue Using The Detection Of Early Increase In Microvascular Blood Content."

Figure 15:
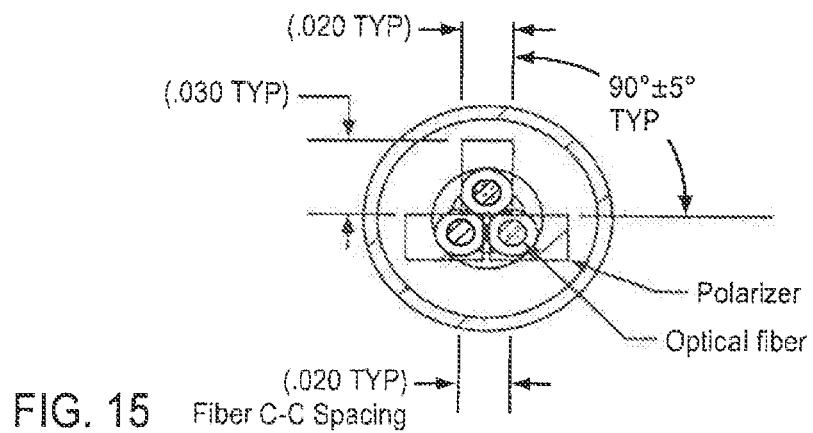
FIG. 15 illustrates in cross section an embodiment of optical fibers and polarizer usable in the optical probe assembly configurations illustrated in any of FIGS. 12, 13, and 14.

FIG. 15 illustrates in cross section an embodiment of optical fibers and polarizer usable in the optical probe assembly configurations illustrated in any of FIGS. 12, 13, and 14.

Figure 16:
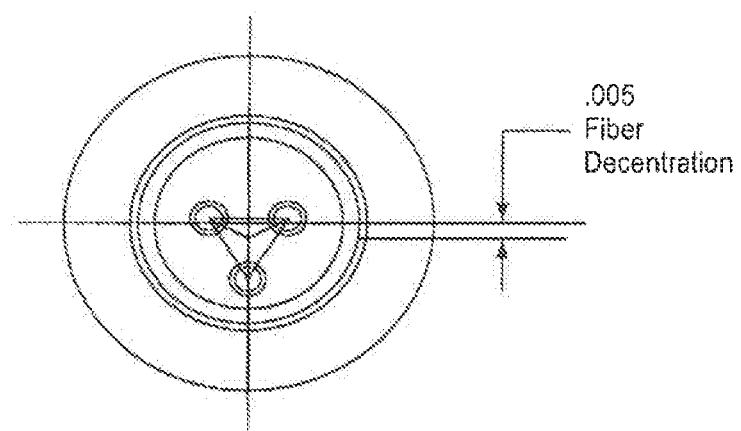
FIG. 16 illustrates in cross section a further embodiment of optical fibers and polarizer usable in the optical probe assembly configurations illustrated in any of FIGS. 12, 13, and 14.

FIG. 16 illustrates in cross section a further embodiment of optical fibers and polarizer usable in the optical probe assembly configurations illustrated in any of FIGS. 12, 13, and 14, and shows a decentering or making the fibers slightly asymmetric with respect to the probe center to minimize reflections. This could be used on any probe designs that detect EIBS described herein.

As discussed above, converting the bench top configurations shown in FIGS. 1A and 1B into a fiber optic probe is possible, but would require several detectors to sample sampling the entire two-dimensional plane of the LEBS peak, such as by a fiber bundle or a two-dimensional array of detectors. Due to the resulting size and cost, the bench top configurations are not necessarily ideal for use in a probe for in vivo measurement.

However, the inventors have developed alternative configurations for an accurate, efficient, and cost effective LEBS fiber optic probe. Because un-polarized light results in a symmetrical LEBS peak, information about the reduced scattering coefficient may be obtained solely by detecting the signal from a few backscattering angles within the LEBS intensity cone. Thus, an LEBS probe needs to acquire the LEBS signal for as few as two backscattering angles within the LEBS intensity cone with respect to each collection fiber. The selection of the angles is based on the concept that one fiber should measure the incoherent baseline (i.e., the diffuse background), while the other(s) measure enhanced backscattering intensity cones, thus giving one parameter which has information about the LEBS peak. This can be achieved by the collinear alignment of fibers as shown in FIG. 17A, also referred to as a collinear fiber assembly.

Figure 17A:
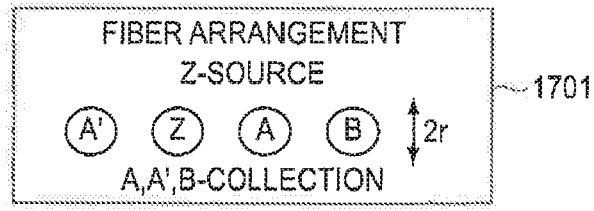
FIG. 17A shows a collinear fiber assembly for use with an LEBS probe.
Figure 17B:
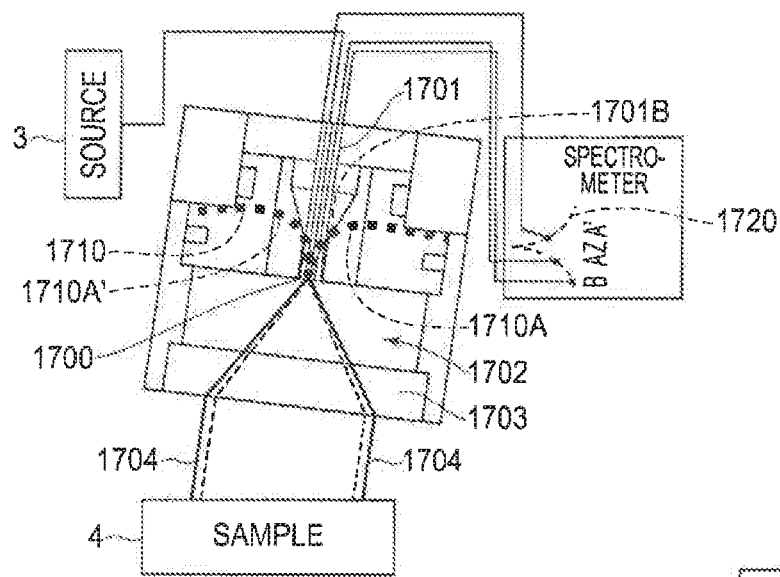
FIGS. 17B and 17C illustrate a collinear fiber assembly used in embodiments of a lens-based LEBS probe and a lens-free LEBS probe, respectively.
Figure 17C:
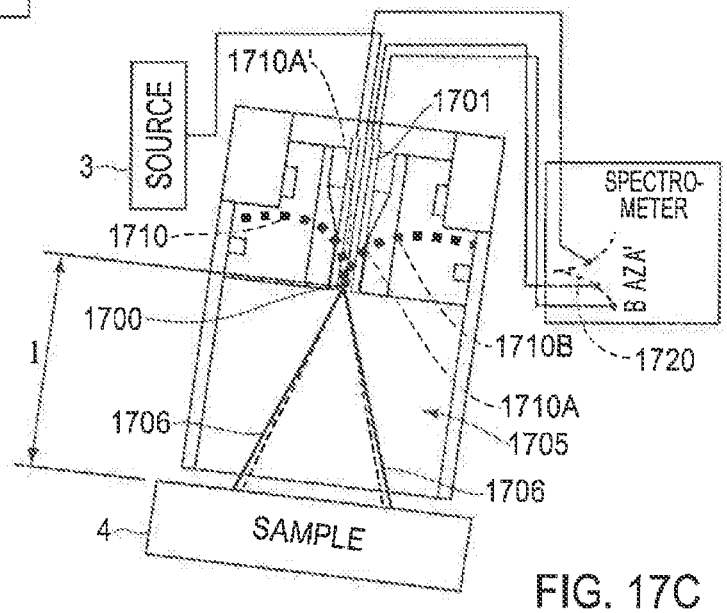

FIG. 17A shows a collinear fiber assembly 1701 for use with an LEBS probe. FIGS. 17B and 17C illustrate a collinear fiber assembly 1701 used in embodiments of a lens-based LEBS probe and a lens-free LEBS probe, respectively. FIG. 17A shows detector fibers A', A, and B in an array surrounding light source fiber Z. In the embodiment depicted in FIG. 17A, detector fibers A' and A detect enhanced backscattering angles, and fiber B collects an incoherent baseline. The collinear fiber assembly 1701 is superimposed at the light source plane 1700 similar to the setups shown in FIGS. 1A and 1B, with the beam splitters eliminated, which results in the formation of the LEBS peak in the retro-reflection direction. The cross section of a probe configured with a collinear fiber assembly 1701 for LEBS spectroscopy is depicted in FIGS. 17B and 17C for lens-based and lens-free LEBS fiber optic probes, respectively. In the lens-based LEBS probe geometry shown in FIG. 17B, broadband light source 3 is connected to the light source fiber Z in the collinear fiber assembly 1701. Broadband light from light source 3 travels through air gap 1702 and is collimated by lens 1703. The collimated light is relayed to the sample 4. Backscattered light returns through the same optical path 1704 to detector fibers A, A', and B in the collinear fiber assembly 1701, where it is detected in the retro-reflective direction at the light source plane 1700. As described herein, with respect to a preferred embodiment, fibers A' and A detect enhanced backscattering angles, and fiber B collects an incoherent baseline.

In the lens-free LEBS probe geometry shown in FIG. 17C, broadband light source 3 is connected to the light source fiber Z in the collinear fiber assembly 1701. Broadband light from source 3 travels through optical spacer 1705, which can be, for example, a glass rod, of length 1 and diverges on sample 4. Backscattered light returns through the same optical path 1706 to detector fibers A, A', and B in the collinear fiber assembly 1701, where it is detected in the retro-reflective direction at the light source plane 1700. As described herein, detector fibers A, A', and B collect several backscattering angles.

The embodiments shown in FIGS. 17B and 17C may be incorporated into an integral probe apparatus, or alternatively may be incorporated into a probe apparatus comprising a tip assembly releasably connectable to a trunk assembly as described elsewhere in this application.

In the setups shown in FIGS. 17B and 17C, Channel Z (light source fiber) is connected to the broadband light source 3. The LEBS peak forms at the plane of the illumination fiber 1710 and is detected by the detector fiber array (A', A & B) placed collinearly to the plane of the illumination fiber 1710. Channels A and A' sample 0.6±0.24 degrees on either side of the peak, 1710A and 1710A'. Channel B samples 1.18±0.24 degrees, 1710B, which is approximately the incoherent baseline. Thus, the three LEBS intensities detected from the backscattering angles in the two-dimensional peak are mapped onto the spectrometer to give the intensity profile 1720. The intensities collected by Channels A, A' and B are defined by Equations (2) and (3):

$$I_{A,A'}(\Theta=\pm 0.6°,\lambda)=E(\Theta=\pm 0.6°,\lambda)+I_{Diffuse}(\Theta=\pm 0.6°,\lambda) \quad (2)$$

$$I_B(\Theta=1.18°,\lambda)=I_{Diffuse}(\Theta=1.18°,\lambda) \quad (3)$$

where $I_{Diffuse}(\Theta, \lambda)$ is the diffuse intensity and $E(\Theta, \lambda)$ is the LEBS interference signal denoting a rise above the diffuse baseline ($I_{Diffuse}$), both for certain collection angles $\Theta$. Also, since:

$$I_{Diffuse}(\Theta=\pm 0.6°,\lambda) \approx I_{Diffuse}(\Theta=1.18°,\lambda) \quad (4)$$

the LEBS signal (E—rise above diffuse baseline at $\Theta=\pm 0.6°$) can be obtained by the subtraction of Equation (3) from Equation (2) as given in Equation (5):

$$E(\Theta=\pm 0.6°,\lambda)=I_{A,A'}(\Theta=\pm 0.6°,\lambda)-I_B(\Theta=1.18°,\lambda) \quad (5)$$

Figures 18A, 18B, 18C:
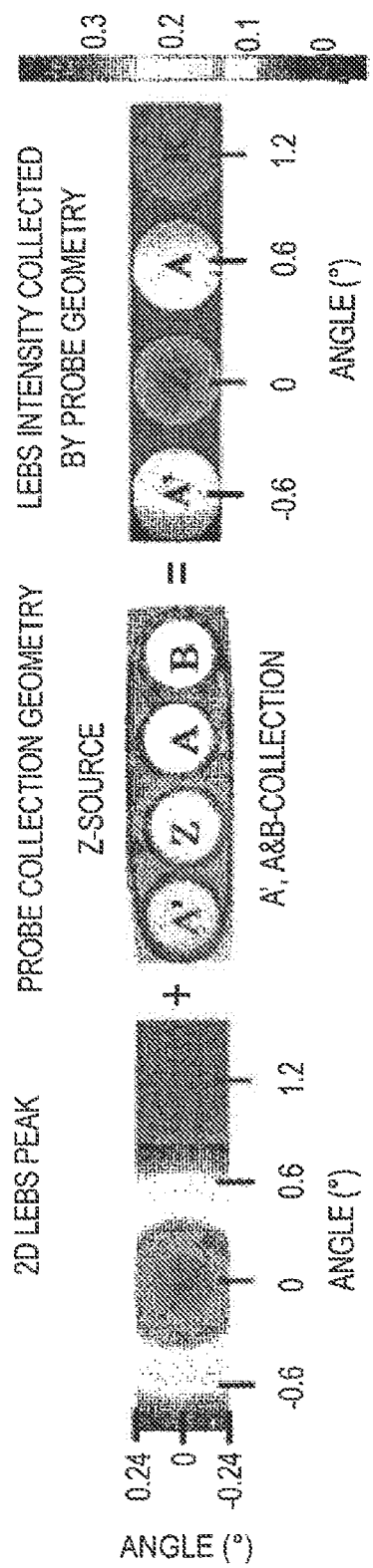
FIG. 18A shows a two-dimensional LEBS peak for a white reflectance standard with LSC of 27 µm at 680 nm obtained from an ex vivo LEBS system.
FIG. 18B illustrates the geometry of a collinear fiber assembly embodiment.
FIG. 18C shows an LEBS intensity profile obtained by superimposing the collinear fiber assembly geometry over the two-dimensional LEBS peak.

As an example, FIG. 18A shows the two-dimensional LEBS peak from a white reflectance standard obtained from the bench top system setup shown in FIGS. 1A and 1B. When the collinear fiber detection geometry shown in FIGS. 1A and 18B is superimposed over the LEBS collection from the two-dimensional peak of FIG. 18A, the result is an angular intensity distribution profile as shown in FIG. 18C. The intensities are the specific LEBS backscattering cone intensities captured by the probe collection fibers at particular angles. While FIG. 18C shows each collection fiber in two dimensions, the actual intensity captured through an LEBS probe fiber with a collinear assembly is an average of the collection angles for each fiber. Note that the probe does not collect a signal through Channel Z, as Channel Z is connected to the light source. Thus, a fiber optic probe measuring LEBS captures three intensity values as represented in FIG. 18C, instead of the entire two-dimensional peak as was the case in ex vivo LEBS observation using the bench top system described above (FIG. 18A). The LEBS peak is formed due to the interference of time-reversed photons above the incoherent (diffuse) baseline, as represented by Equations (2) and (3) and shown in FIG. 18A. LEBS intensity at each angle on the LEBS peak is sensitive to various optical properties, and represents a particular penetration depth. The two-dimensional ex vivo bench top system collects the entire peak. On the other hand, a preferred embodiment of a fiber optic probe measuring LEBS as described herein collects backscattering intensity angles at±0.6±0.24 (A and A') and 1.18±0.24 (B) degrees (Equations (2), (3), and (5)). Information collected by such a probe is sufficient to experimentally measure in vivo the depth-limited reduced scattering coefficient for diagnostics.

To verify the sufficiency of such information, LEBS signal intensities collected via probe geometry of the preferred embodiment described above were modeled with the Mie Monte Carlo (Mie MC) simulation, as reported in V. Turzhitsky, J. D. Rogers, N. N. Mutyal, H. K. Roy, and V. Backman, "Characterization of light transport in scattering media at sub-diffusion length scales with Low-coherence Enhanced Backscattering," IEEE J. Sel. Top. Quantum Electron. 16(3), 619-626 (2010), the entire contents of which are incorporated by reference. A slab of a medium composed of polystyrene beads in water was used. The code collected only small-angle backscattered rays from 0° to 10° most suitable for modeling backscattering, and the Mie phase function was used in MC to obtain the probability distribution of backscattered light (P(r)). The two-dimensional LEBS peaks were obtained by numerically computing the Fourier transform of P(r)*C(r) from Equation (1).

Figure 19A:
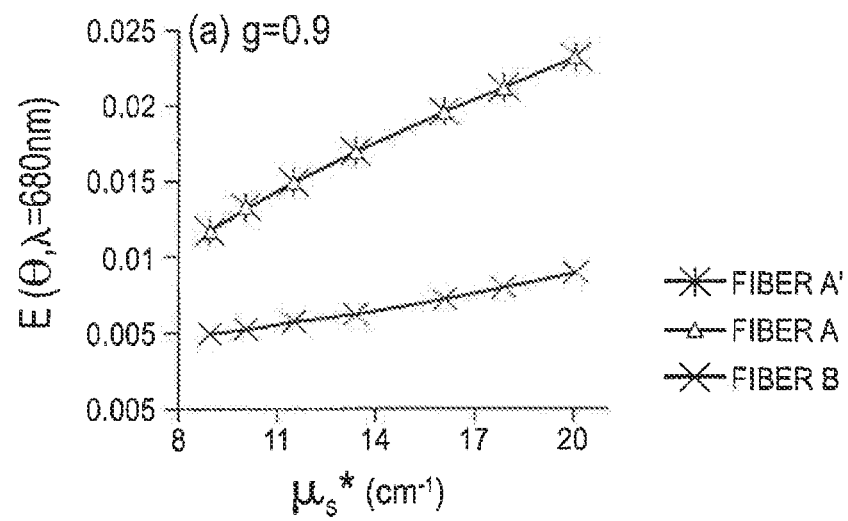
FIGS. 19A and 19B show the LEBS intensities and Diffuse Reflectance intensities, respectively, collected by various detection fibers of the probe geometry simulated by MC.
Figure 19B:
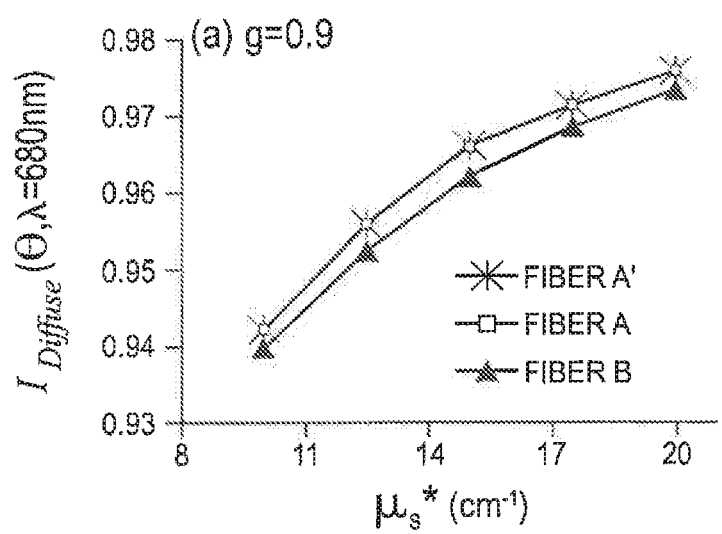

FIGS. 19A and 19B show the LEBS intensities and Diffuse Reflectance intensities, respectively, collected by various detection fibers of the probe geometry simulated by MC. The average LEBS intensities (E(Θ, k)) obtained from the peak simulated by Mie MC were collected at the same angles as the probe detection fibers (±0.6°±0.24 for A & A' & 1.8°±0.24 for B) of the preferred embodiment, as shown in FIG. 19A. FIG. 19B shows the Diffuse Reflectance intensities collected by the same fibers have similar intensities when the interference signal is absent ($L_{SC}=0$).

Since the LEBS peak is rotationally symmetric for unpolarized illumination, the intensities of fibers A and A' collecting ±0.6±0.24° are exactly the same. Fibers A and A' collecting LEBS intensity near the peak (±0.6±2.4°) have higher intensities (nearly 3 times) compared to fiber B collecting the incoherent baseline away from the peak (1.18±0.24°). The intensities are proportional to $\mu_s^*$. The foregoing confirms that the intensities collected by fiber geometry measure part of the LEBS signal, and these signals are sensitive to optical properties ($\mu_s^*$ and g).

The lens-free LEBS probe of the preferred embodiment described herein provided the first known observation of LEBS. Additionally, the lens-free LEBS probes disclosed herein have the ability to measure depth-limited optical properties from the low-coherent EBS intensity.

In order for the coherent intensity to occur, it is necessary to have partial coherence of light (coherence length $L_{SC} \ll l_s^*$). Conventional probes to not attain partial coherence of light due to at least the large radius of fiber (radius is inversely proportional to $L_{SC}$). In addition, the fibers need to be placed in very close proximity to detect the enhanced intensity observed at smaller angles. Lens-free LEBS probes as disclosed herein overcome both these engineering challenges by, for example, 1) employing a fiber with a smaller radius, and preferably fibers having a core+cladding diameter of about 20-100 μm, and more preferably a core+cladding diameter of about 60 μm; 2) placing fibers in very close proximity, and preferably a center-to-center spacing of about 20-200 μm, and more preferably a center-to-center spacing of about 60 μm; and 3) isolating the interference signal above diffuse intensity ($I_A-I_B$ from Equation (5)). As a result, lens-free LEBS probes of the present disclosure offer superior performance over contemporary probes, such as contemporary DRS probes.

Experimental data has confirmed the superior performance of lens-free LEBS probes as disclosed herein. For example, the DRS signal obtained from a lens-free LEBS probe of a preferred embodiment was modeled using MC code based on code developed by Ramella-Roman et al. (J. C. Ramella-Roman, S. A. Prahl, and S. L. Jacques, "Three Monte Carlo programs of polarized light transport into scattering media: part II," Opt. Express 13(25), 10392-10405 (2005)), and then the illumination collection geometry of the lens-free LEBS probe of a preferred embodiment was simulated to quantify the behavior of the average penetration depth and diffuse reflectance signal in relation to the optical properties of the medium. Unlike the MC described earlier (FIG. 19A), this MC did not take into account any interference effect—only diffuse intensity collection from the same geometry.

The lens-free geometry of the LEBS probe used for these experiments is shown in FIGS. 17C and 18C. At the junction of the glass rod and sample, the incoming light beam had a diameter of about 0.26 cm based on the overall length of the glass rod 12 (l=9 mm) and the numerical aperture (NA) of the illumination fiber (0.22). In the MC code, the initial entry x-y coordinate of a photon into the medium is randomly selected from within this 0.26 cm diameter illumination area. For simplicity, the illumination fiber was considered to be a point source such that the entry angle of a photon can be computed directly from the initial entry x-y coordinate and the length of the glass rod. Light propagation within the medium is determined by the scattering coefficient ($\mu_s$), the absorption coefficient ($\mu_a$), and the properties of the phase function. A Mie phase function was used for these simulations, as described in V. Turzhitsky, J. D. Rogers, N. N. Mutyal, H. K. Roy, and V. Backman, "Characterization of light transport in scattering media at sub-diffusion length scales with Low-coherence Enhanced Backscattering," IEEE J. Sel. Top. Quantum Electron. 16(3), 619-626 (2010).

Simulations were performed for g=0.9 and $\mu_s=[100-200$ cm$^{-1}$]. When a photon reached the junction of the glass rod and the sample, its trajectory was traced to the collection fiber plane at the other end of the glass rod. A photon was considered collected if it intercepted a collection fiber within the NA of the fiber (NA=0.22). Reflectance intensity was recorded for each collection fiber separately. Boundary reflection between the glass rod (n=1.52) and the sample (n=1.33) was handled through Fresnel equations. Ten million photons were tracked for each simulation. The normalized diffuse intensity obtained from these MC simulations is plotted in FIG. 19B. As expected, when coherence is not present the DR intensities collected by the fibers (A, A'&B) of the probe are very similar, indicating the absence of enhanced backscattering. Also, in the case where coherence in present, as depicted by Equation (6):

$$\frac{E(\Theta = \pm 0.6°, \lambda)}{I_{Diffuse}(\Theta = \pm 0.6°, \lambda) - I_{Diffuse}(\Theta = 1.18°, \lambda)} > 4 \qquad (6)$$

the dominant signal is the signal of enhanced backscattering. This demonstrates that conventional probes, which do not have a condition for finite spatial coherence, do not detect enhanced signals, whereas lens-free LEBS probe of the present disclosure (e.g., probe geometry as described by Equations (5) and (6)) detect enhanced signals.

Although lens-based LEBS probes and lens-free LEBS probes described herein measure identical LEBS peaks, lens-free LEBS probes are preferred due to its advantages, including superior signal-to-noise ratio (SNR), ease of manufacture, ease of component alignment, reduced maintenance requirements, and lower cost. The background reflection intensity of each LEBS probe was measured by pointing the probe at a dark corner of the room.

Figure 20A:
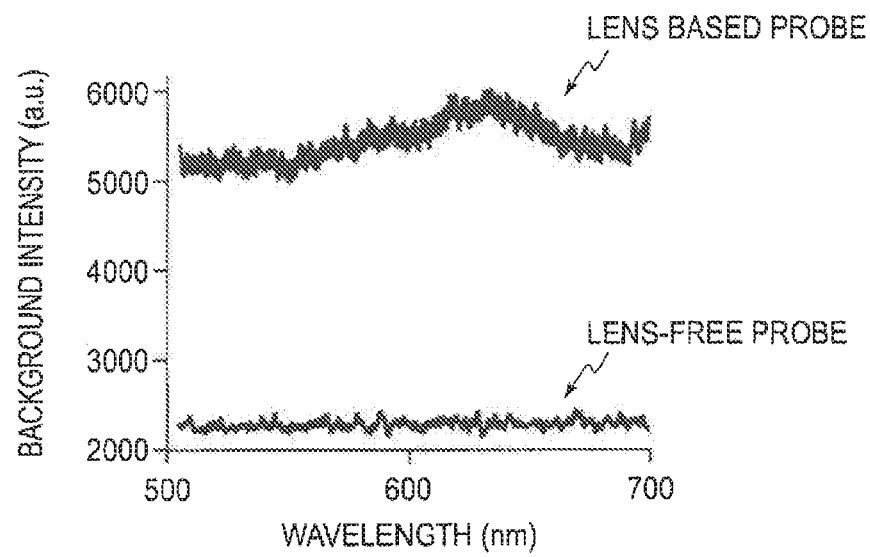
FIG. 20A shows the background intensity observed with prototype lens-based and lens-free LEBS probes.
Figure 20B:
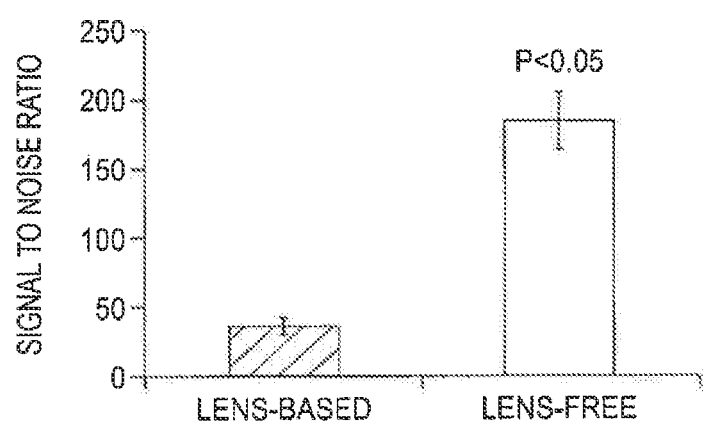
FIG. 20B shoes the Signal-to-Noise Ratio for a white reflectance standard for prototype lens-based and lens-free LEBS probes.

FIG. 20A shows the background intensity observed with prototype lens-based and lens-free LEBS probes. FIG. 20B shows the Signal-to-Noise Ratio for a white reflectance standard for prototype lens-based and lens-free LEBS probes. FIG. 20A shows that the reflection of the lens-based LEBS probe was about twice as high compared to the lens-free LEBS probe. The increased reflection in the lens-based LEBS probe is attributed to the presence of air gap 10 in the probe tip, between lens 11 and the collinear fiber assembly. The increased reflection lowers the SNR of the lens-based LEBS probe. On the other hand, incorporation of a refractive index-matched glass rod in the lens-free LEBS probe results in significantly less reflection.

The SNR of lens-based LEBS probes and lens-free LEBS probes were evaluated by measuring $I_A-I_B$ (Equation (5))

from a white reflectance standard (Spectralon, Labsphere Inc., N.H.). The lens-free LEBS probe had four times the SNR as compared to a lens-based LEBS probe (FIG. 20B).

Multiple embodiments of LEBS probe assemblies are described below. Although these embodiments are shown as comprising a disposable tip assembly that releasably connects to a reusable trunk assembly, the embodiments are not limited to a detachable configuration, and may be used in a probe assembly in which, as an example, the tip is integral with the trunk assembly, or in which other components of the probe assembly are releasable. Additionally, the principles and concepts described elsewhere in this application may be incorporated into the following demonstrative embodiments.

Figure 21:
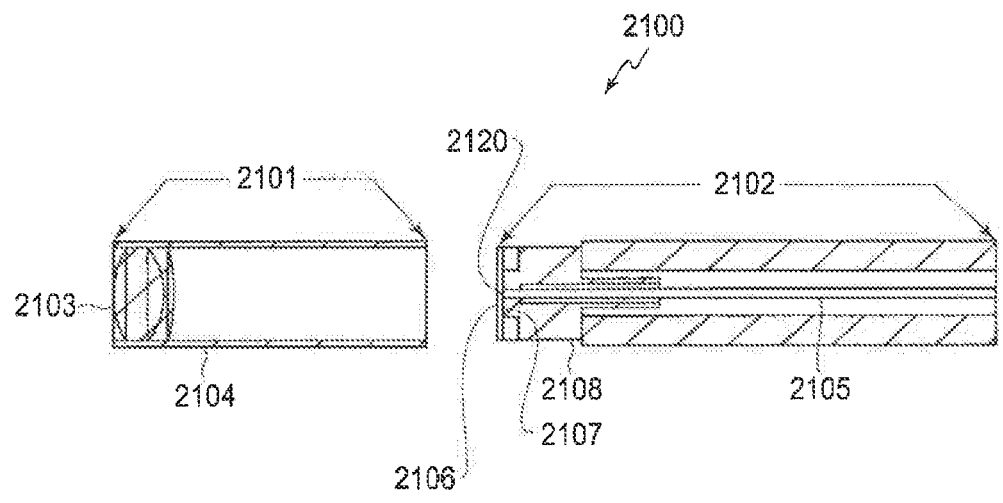
FIG. 21 illustrates a particular optical probe assembly configuration used for LEBS.

FIG. 21 illustrates an embodiment of an optical probe assembly 2100 configuration used for LEBS. The embodiment shown in FIG. 21 comprises a disposable tip assembly 2101 configured to releasably connect to the reusable trunk assembly 2102. The tip assembly 2101 features an achromatic doublet lens 2103 held by a lens mount 2104 and positioned at an end of the tip opposite from an end that connects to the trunk assembly 2102. In preferred embodiments, the focal length of the achromatic doublet lens 2103 is about 6 mm, and is assembled at a distance of about 6 mm from the end-face 2120 of the optical fibers 2105, i.e., the plane of the illumination fiber, held in place by fiber mount 2108. The trunk assembly 2102 houses the collinear fiber assembly 2105, and optionally includes a protective cover 2106 and polarizer 2107 at an end of the trunk assembly 2102 that connects to the tip assembly 2101. The opposite end of the trunk assembly (not shown) is configured to connect to a broadband light source and a spectrophotometer (also not shown), and may branch out into multiple portions for, as an example, each fiber optic channel.

Preferred embodiments use four optical fibers with a core diameter of about 20-100 µm, and more preferably about 50 µm; and a core+cladding diameter of about 30-90 µm, and more preferably about 60 µm. In a four-fiber assembly, one fiber is used for illumination, and the remaining fibers are used for signal collection. Preferably, the fibers in the fiber assembly are arranged in a linear array, resulting in a fiber center-to-center spacing, i.e., space between neighboring fibers, of about 20-100 µm, and more preferably about 60 µm.

Figure 22:
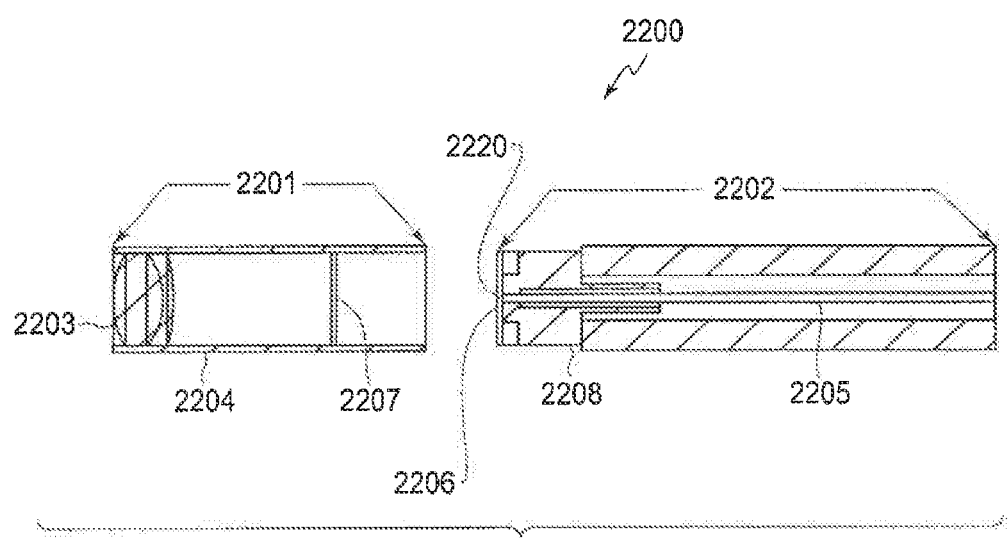
FIG. 22 illustrates another particular optical probe assembly configuration used for LEBS.

FIG. 22 illustrates another embodiment of an optical probe assembly configuration used for LEBS. The embodiment shown in FIG. 22 is similar to the embodiment shown in FIG. 21, except that the polarizer 2206 is located on the disposable tip assembly 2201 instead of the reusable trunk assembly 2202.

Figure 23:
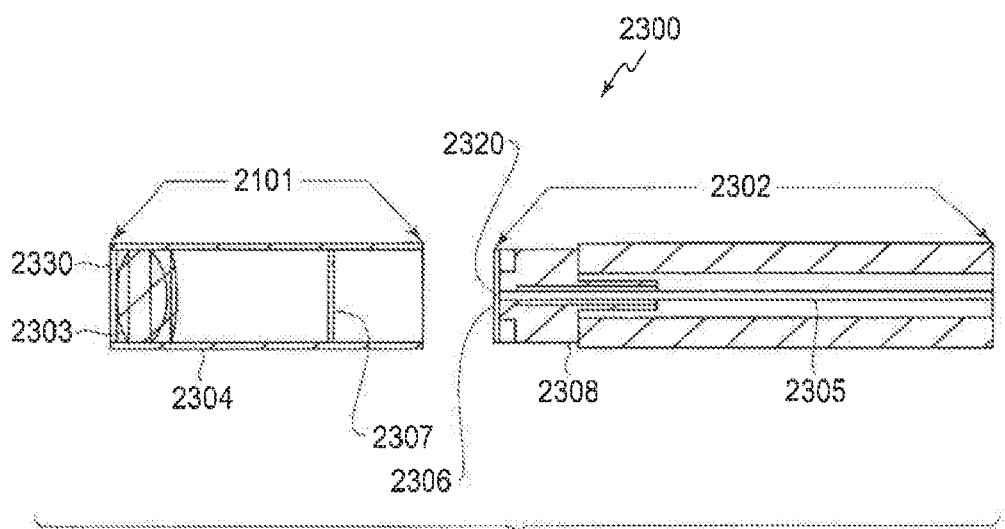
FIG. 23 illustrates a further particular optical probe assembly configuration used for LEBS.

FIG. 23 illustrates an embodiment of an optical probe assembly configuration used for LEBS. The embodiment shown in FIG. 23 is similar to the embodiment shown in FIG. 22, except that the disposable tip assembly 2301 also features a transparent spacer 2330.

Figure 24:
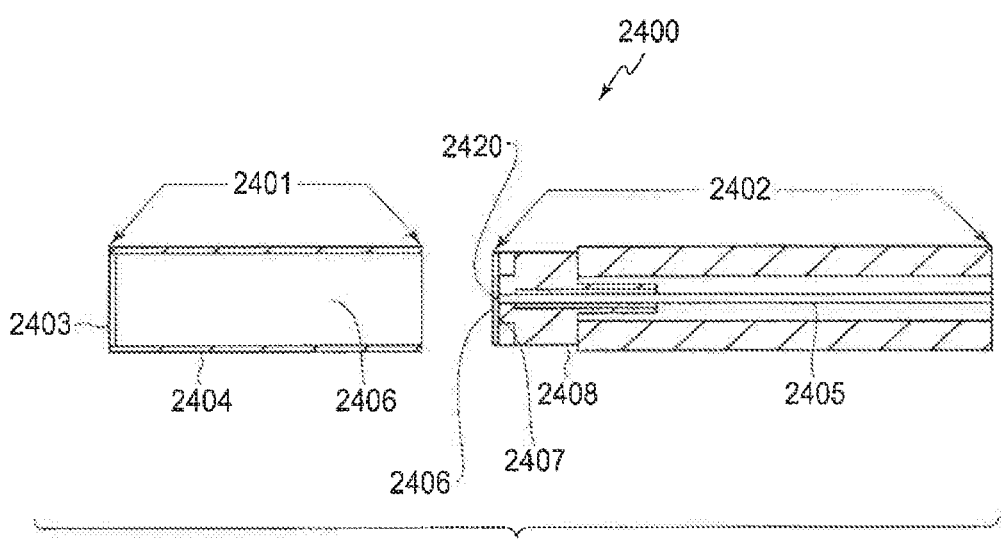
FIG. 24 illustrates a further particular optical probe assembly configuration used for LEBS.

FIG. 24 illustrates another embodiment of an optical probe assembly configuration used for LEBS. In this embodiment, the optical component of the disposable tip assembly comprises a transparent cover slide 2403 held by cover slide mount 2404, and a gap 2406 filled with air or another fluid.

Preferred embodiments of lens-free LEBS probes use four optical fibers with a core diameter of about 20-100 µm, and more preferably about 50 µm; and a core+cladding diameter of about 30-110 µm, and more preferably about 60 µm. In a four-fiber assembly, one fiber is used for illumination, and the remaining fibers are used for signal collection.

Preferably, the fibers in the fiber assembly are arranged in a linear array, resulting in a fiber center-to-center spacing, i.e., space between neighboring fibers, of about 20-220 µm, and more preferably about 60 µm.

Figure 25:
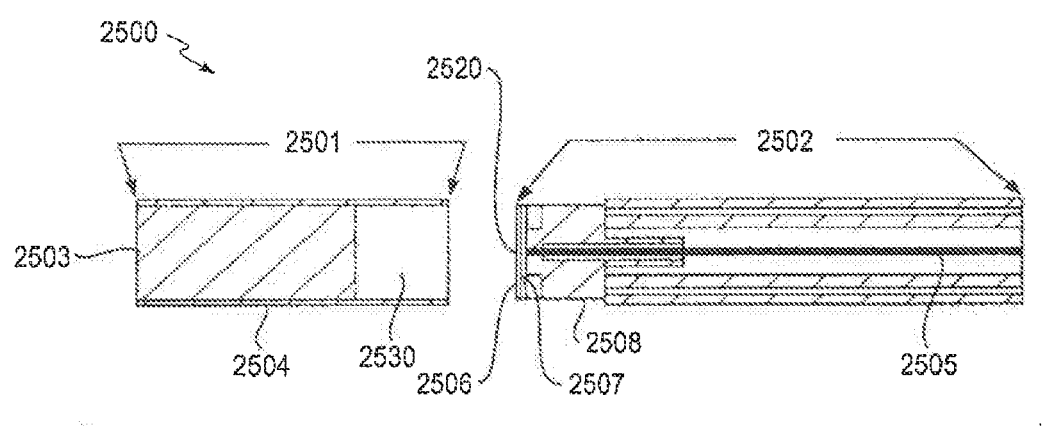
FIG. 25 illustrates a further particular optical probe assembly configuration used for LEBS.

FIG. 25 illustrates another embodiment of an optical probe assembly configuration used for LEBS. In this embodiment, the disposable tip assembly 2501 features a transparent rod 2503 as an optical spacer, held by rod mount 2504. Space 2530 is provided for insertion of an end of the trunk assembly 2502. The embodiments shown in FIGS. 24 and 25 are lens-free, i.e., the tip assembly features an air gap and coverglass (FIG. 24) or transparent rod (FIG. 25) or other optical spacer, such as a glass spacer or plastic spacer, instead of a lens.

Preferably, the glass rod has an index of refraction value of approximately 1.5, and a length of about 9 mm. Alternatively, an optical grade plastic rod with an index of refraction value of approximately 1.5, and a length of about 9 mm, may be used.

In the embodiments described above, when the tip assembly is connected to the trunk assembly, the position of the optical component(s) of the tip assembly relative to the fiber terminations and the tissue results in a specific spatial coherence length that corresponds to a desired measurement depth. Thus, the tip assembly and optical component(s) are configured for a predetermined spatial coherence length. In the lens-free embodiments, a fixed-distance spacer can be used to establish the spatial coherence length.

Additionally, the optical component(s) may be split between the tip assembly and the trunk assembly. For example, the optical spacer in a lens-free LEBS probe may be split such that the tip assembly houses one part of the spacer, and the trunk assembly (or other component of the probe apparatus) houses another part of the spacer. The optical spacer may be split into more than two parts, such that more than two elements of the probe apparatus are connected to form the complete optical path and achieve the desired penetration depth.

Figure 26:
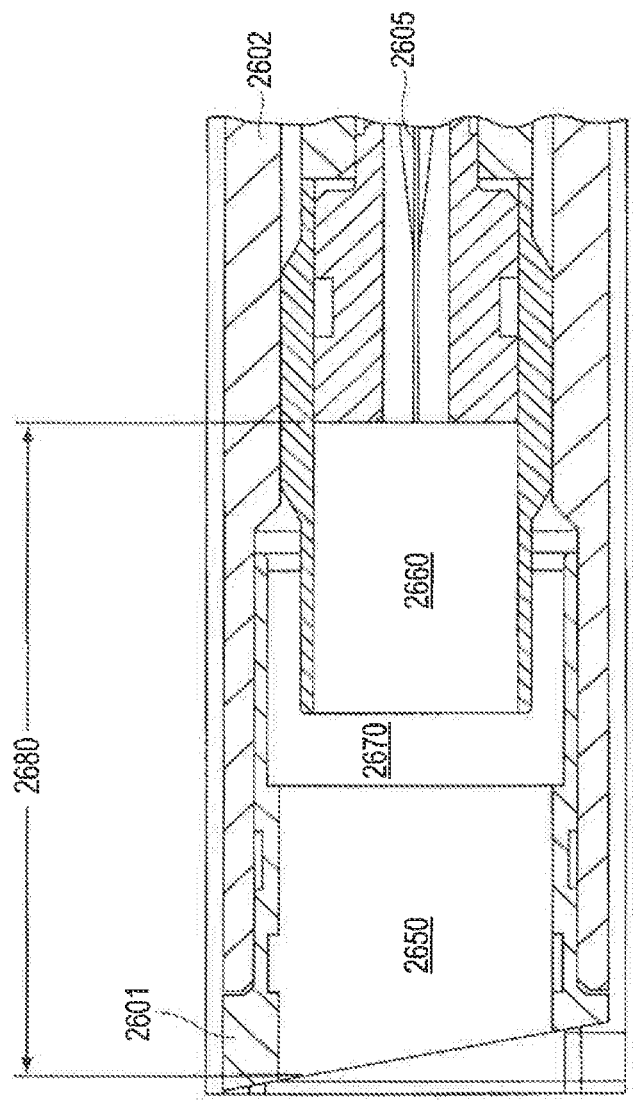
FIG. 26 shows an embodiment of an LEBS probe in which a part of the optical spacer is housed in the tip assembly, and a part of the optical spacer is housed in the trunk assembly.
Figure 28A:
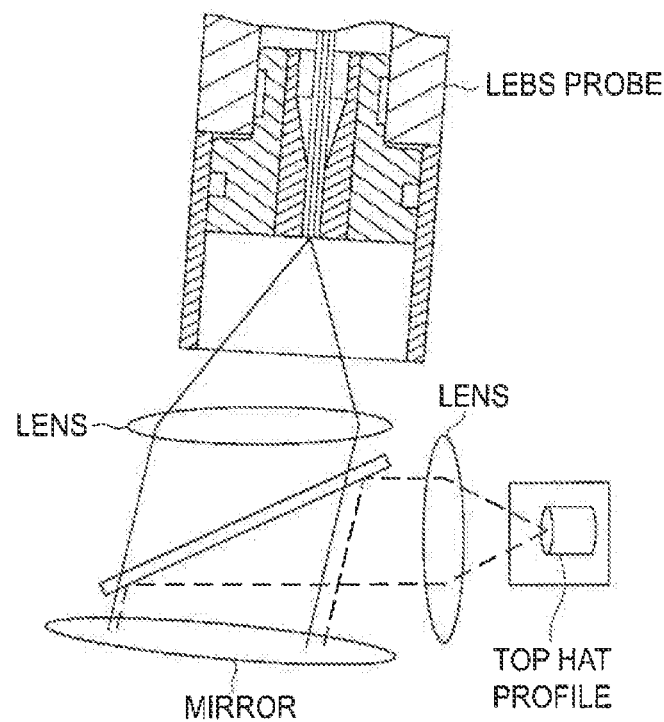
FIG. 28A shows the configuration used for measurement of C(r) of the source (Z) channel of the a prototype lens-free LEBS probe.
Figure 28B:
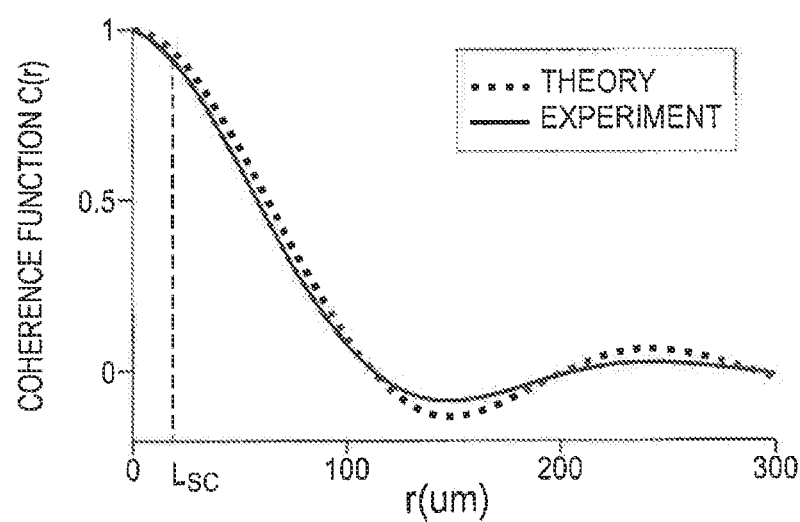
FIG. 28B shows the results of the experimentally observed C(r) from the prototype compared to the theoretical C(r).

FIG. 26 shows an embodiment of an LEBS probe in which a part of the optical spacer 2650 is housed in the tip assembly 2601, and another part of the optical spacer 2660 is housed in the trunk assembly 2602. When the tip assembly and the trunk assembly are connected, the parts of the optical spacer join to form a single optical path 2680. The dimensions of the parts of the optical spacer are selected to achieve a desired optical path length, thereby setting the spatial coherence length and the resulting measurement penetration depth. Alternatively, the probe apparatus may have multiple elements can be used in various combinations, thereby providing the ability to easily change the penetration depth.

The lens-based embodiments demonstrate exemplary optical component configurations, including various combinations of components can be used. However, LEBS probe assemblies are not limited to the specific embodiments disclosed herein, and may feature other combinations of components, may or may not have polarizers or spacers, and may feature different numbers of optical fibers. Further, embodiments may feature a tip assembly integral with the trunk assembly.

FIGS. 27A-27D illustrate an embodiment of a lens-free LEBS fiber optic probe 2700 with a glass rod 2703 attached to a glass ferrule 2704, with a collinear fiber assembly 2705 containing four fibers arranged collinearly. FIG. 27A shows a fully assembled LEBS fiber optic probe. FIG. 27B is a cross-section of the probe embodiment, and FIGS. 27C and 27D are the z-y and x-y cross sections, respectively, of the probe embodiment. The illustrated length of the LEBS fiber optic probe configuration in FIGS. 27A and 27B is shortened for illustrative purposes. In a preferred embodiment, the outer diameter of the probe is about 3.4 mm, although the outer diameter may be different for various reasons, such as compatibility with a pre-existing reusable trunk assembly or endoscopic instrument channel. The overall length of the fiber optic probe, i.e., tip assembly and trunk assembly, is about 3 meters. The probe also features a rigid potion 2750 approximately 1.54 cm in length. Of course, these lengths may vary. Instead of using a beam splitter to separate the illumination (FIGS. 1A and 1B) from detection angles, the angles were combined in a compact tubing with an outer diameter of 3.4±0.1 mm, resulting in the geometrical arrangement of the illumination and collection fibers as shown in FIG. 18B. The LEBS peak therefore forms at the plane of the illumination fiber. As shown in FIGS. 18B and 27, the probe includes four adjacent optical fibers (each fiber being glass/glass/polyimide/acrylate 50/60/70/160 µm diameter, 0.22 NA) and a BK7 glass rod (length=9±0.1 mm, refractive index=1.51).

The fibers (Polymicro Tech., Ariz.) of the collinear fiber assembly are arranged in a linear array within a custom extruded glass ferrule 2704, connected by an adhesive, such as an epoxy, or cement, and preferably a non-optical path epoxy within the fiber ferrule, and polished flat on the aligned fiber end faces, as shown in FIG. 27C. The polished fiber endface is then attached to the spacer. The buffer and jacket are removed from the fiber ends (within the glass ferrule) prior to installation in order to provide a 60±3 µm nominal center-to-center spacing. In order to reduce specular reflections, the distal tip of the glass rod 2703 is beveled to about 4°-10°, and preferably to about 9.5°.

The average penetration depth, as well as the measurement of enhanced backscattering intensity cone, is governed by the selection of $L_{sc}$. It is therefore necessary to control $L_{sc}$ to obtain depth selectivity. According to the Van Cittert-Zernike theorem, the spatial coherence length ($L_{sc}$) of:

$$L_{SC} = \frac{\lambda l}{2\pi rn} \quad (7)$$

Light can be tuned by setting the core radius of the fibers (r), length of the glass rod (l), and/or refractive index of the glass rod (n). The illumination fiber was coupled to a 35 W Xenon lamp (HPX 2000, Ocean Optics, FL) and the three collection fibers were coupled to three miniature fiber spectrometers (USB 2000+, Ocean Optics, FL).

$$C(r) = \frac{2J_1 \frac{r}{L_{SC}}}{\frac{r}{L_{SC}}} \quad (8)$$

The experimentally measured $L_{SC}$ was determined to be ~27 µm, which matches the $L_{SC}$ calculated by Equation (7). It should be noted that the probe needs to be used in contact mode to attain this $L_{SC}$, i.e, the measurement is taken from a target surface when the probe tip is in contact with that surface for measurements at this $L_{SC}$.

Since this embodiment is lens-free, the beam has an $L_{SC}$ of 27 µm at the tip end of the tip assembly, maintained by the length of the glass rod. The beam diverges after that point, and the resultant $L_{SC}$ changes accordingly. In addition to the specific lens-free LEBS probe embodiment discussed above, the inventors have successfully manufactured a lens-free LEBS probe with an $L_{SC}$ of 43 µm (r=25 µm, l=15, outer diameter=5 mm). Further, a lens-free LEBS probe with $L_{SC}$ of 86 µm (r=12.5 um, l=15, outer diameter=5 mm) from off-the-shelf and readily available components is contemplated.

Experimental results have verified the capability of building a probe based on the principle of collecting three backscattering angles to measure $\mu_s^*$ with LEBS. The experiment used a phantom to mimic the optical properties of tissues of varying $\mu_s^*$ with constant g. The phantom was prepared by mixing polystyrene beads (Thermo Fisher, Conn.) in water to attain certain $\mu_s^*$ and g (the mixing ratios were determined by Mie theory). The readings of LEBS intensities were obtained by measurement of these phantoms with the prototype lens-free fiber optic probe. The choice of the polystyrene bead phantoms is attractive since their scattering behavior is governed by Mie theory and the inventors have developed Mie MC simulations for simulating the LEBS peak obtained in two-dimensions from these phantoms. These two-dimensional LEBS peaks obtained from Mie MC simulations have been validated by matching them to experimentally observed two-dimensional peaks from ex vivo systems.

Figure 29A:
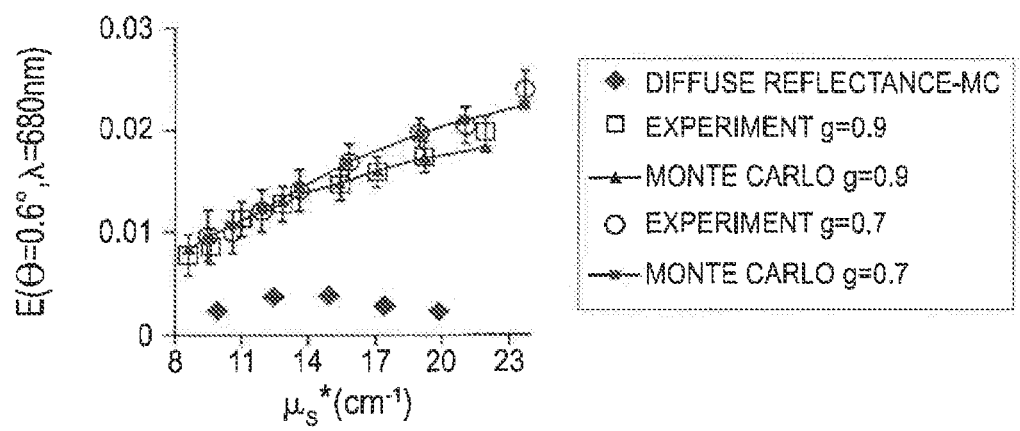
FIG. 29A shows the experimental LEBS intensity (E(Θ, λ)) for a prototype lens-free LEBS probe compared to theoretical LEBS intensity and Diffuse Reflectance.
Figure 29B:
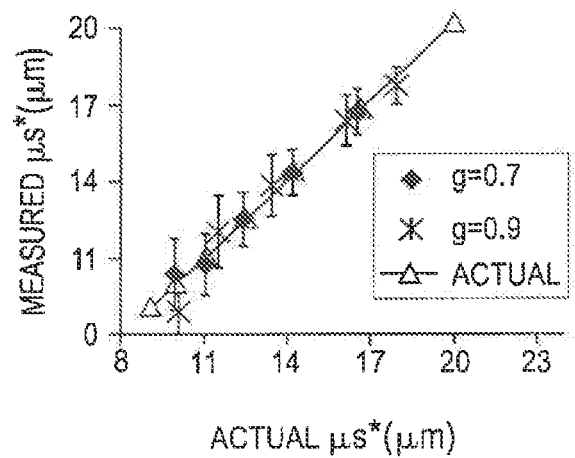
FIG. 29B is an independent validation curve comparing actual and measured reduced scattering coefficients, $\mu_s^*$.

The LEBS intensities measured experimentally from the prototype LEBS probe can be matched with the MC simulation by analyzing the same angles as collected by the probe. This approach serves as a gold standard test for verifying whether the prototype probe measures LEBS. The LEBS interference intensity $E(\Theta=0.6°,\lambda)$, which is defined in Equation (5) as the $I_A-I_B$ (obtained after background subtraction and normalization by a spectralon reflectance standard with >98% reflectance) was measured. FIG. 29A shows that the experimental LEBS intensity ($E(\Theta,\lambda)$ for the prototype lens-free LEBS probe closely matches ($R^2$~0.9) the interference (LEBS) MC simulation. The LEBS intensity shows a significant residual signal ($I_A-I_B$) from interference which is directly proportional to $\mu_s^*$, while the diffuse reflectance (DR) MC signal is close to zero with no dependence on $\mu_s^*$. FIG. 29B shows an independent validation curve in which the $\mu_s^*$ measured from phantoms of prescribed optical properties by the probe shows excellent agreement ($R^2$~0.99).

These results demonstrate that the prototype LEBS probe isolates only enhanced backscattering intensity, since the raw intensity from the probe has LEBS and diffuse components in every channel (Equations (2) and (3)), and after subtraction the diffuse component which is equal in both is eliminated (Equations (4) and (5)). The values of this parameter $E(\Theta=0.6°,680$ nm) were matched with prior results from the MC simulation based on Mie theory for LEBS. To calculate $E(\Theta=0.6°,680$ nm) from MC, the collection geometry of the prototype probe was superimposed on the two-dimensional LEBS peak to measure angles corresponding to collection fibers for varying $\mu_s^*$ & g as shown in FIG. 19A. From this MC result, $E(\Theta=0.6°,680$ nm) was calculated from Equation (5) (as $I_A-I_B$), and matched with experimental data obtained from the prototype probe. As shown in FIG. 29A, there is a good match ($R^2$~0.9) between the MC and experimental data after applying a constant multiplicative scaling factor. The corresponding diffuse reflectance signal (DR) defined in Equation (9) is:

$$DR = I_{Diffuse}(\Theta=\pm0.6°,\lambda) - I_{Diffuse}(\Theta=1.18°,\lambda) \quad (9)$$

FIG. 29A includes DR for the prototype LEBS probe. The DR intensity is close to zero, indicating the absence of enhanced intensity along with showing no trend (proportionality) with $\mu_s^*$. This data, shown in FIG. 29A, has three implications: (1) the probe experimentally measures an LEBS signal which matches with the ex vivo setup and MC simulations; (2)) $E(\Theta=0.6°)$ can be used to extract $\mu_s^*$ by using a lookup table; and (3) the diffuse reflectance signal ($I_{Diffuse}(A)-I_{Diffuse}(B)$) obtained from the MC simulation of the prototype LEBS probe has flat dependency with $\mu_s^*$, the value of which is close to zero (not measuring the enhanced intensity signal and hence $\mu_s^*$). To extract $\mu_s^*$ from $E(\Theta=0.6°,680 \text{ nm})$, a lookup table can be constructed using MC data, and then the lookup table can be used to validate the measured optical properties with actual optical properties from an independent set of phantoms. As shown in FIG. 29B, there is a good match between actual $\mu_s^*$ and $\mu_s^*$ measured by the prototype LEBS probe (R2~0.9). Subsequently, fractal dimension ($D_f$) can be calculated by using the dependence of $\mu_s^*$ with $\lambda$ as given by Equation (10):

$$Df = \left(\frac{dE(\Theta = 0.6°, \lambda) * \lambda_c}{d\lambda * E(\Theta = 0.6°, \lambda_c)}\right) 0.4 + 1.5 \qquad (10)$$

where, $\lambda_c$ is the central (average) wavelength.

While the experimental results demonstrate the ability of the LEBS probes disclosed herein to accurately measure scattering optical properties, it is also important to achieve depth selectivity, as the location of abnormal tissue in precancer is limited to the topmost mucosal layer. For example, it is known that epithelial cells, located at the bottom of the colon crypt, can accumulate mutations over a period of years and thus are the initiating cells in colon carcinogenesis. It is therefore crucial to have the ability to optimally probe these changes with a depth-limited measurement. Depth selectivity is an inherent advantage of LEBS, since the LEBS peak is obtained by combining the EBS measurements with low spatial coherence and broadband illumination. Low spatial coherence illumination ($L_{SC}$<ls<<ls*) behaves as a spatial filter that rejects longer path lengths. Therefore, the penetration depth of LEBS photons can be limited by restricting the spatial coherence length of illumination, $L_{SC}$.

The depth dependence of the LEBS enhancement for the two-dimensional peak LEBS can be easily applied to probe geometry. For following discussion relates to the verification and characterization of the dependency of optical scattering properties measured by the prototype LEBS probe with an average penetration depth. For a given optical property, a saturation curve C(T):

$$C(T) = \int_o^T p(Z)dZ \qquad (11)$$

where p(Z) is the probability that light returns from depth Z was constructed for $E(\Theta=0.6°,680 \text{ nm})$ by limiting the maximum depth from which rays were reflected (by modifying the thickness of medium via post-processing of MC data. The normalized derivative (p(Z)=dC/dT) of the saturation curve yielded the probability distribution as a function of depth, p(Z). The average penetration depth ($PD_{avg}$) was then calculated according to the first moment:

$$PD_{avg} = \int zp(Z)dz \qquad (12)$$

Empirically, the average penetration depth (Eq. (12)) can be represented in closed form as:

$$PD_{avg} = a(L_{SC})^{1-b}(ls^*)^b \qquad (13)$$

where:

$$a = a_0 + a_1 g + a_2 g^2$$
$$b = b_0 + b_1(1-g)^{b_2} \qquad (14)$$

Figure 30:
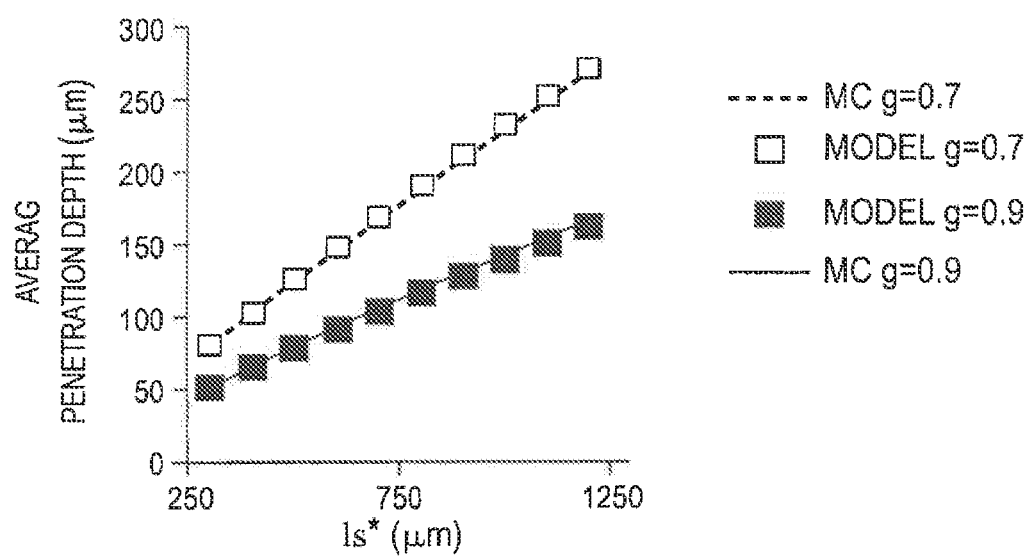
FIG. 30 shows a comparison of the average penetration depth to the theoretical penetration depth calculated using the Mie theory phase function.

The term a and the power b depend on the anisotropy factor g (as described by Equation (14)). The constants are $a_0$=0.54, $a_1$=−0.11, $a_2$=−0.23, $b_0$=0.79, $b_1$=0.24, and $b_2$=0.75. The expressions in Equation (13) and values of the coefficients are obtained empirically by fitting with MC simulations. For tissue, g~0.9 (which yields a=0.26 & b=0.84), the resultant average penetration depth for the probe is 116 µm (with ls*=800). As shown in Equation (13), the average penetration depth of the probe is directly proportional to Lsc and can be limited (by modifying probe geometry) to the required range based on the application. FIG. 30 shows the validation of the accuracy of the equation for a range of ls* and g relevant to a tissue regime by comparing the values of average penetration depth obtained from the equation with MC simulations at Lsc=27 µm. As shown in FIG. 30, good agreement (R2~0.99) is achieved between the two suggesting the validity of the derived equation.

Figure 31A:
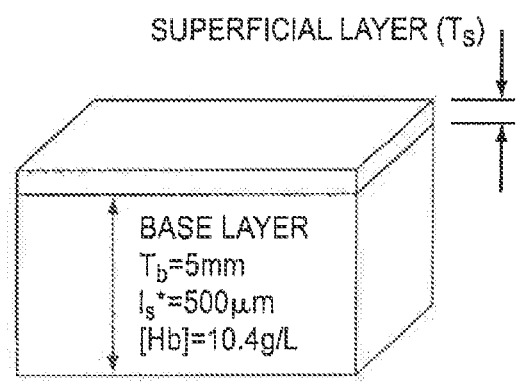
FIG. 31A illustrates a two-layered phantom with a superficial layer and a basal layer.

Experimental verification of the depth-limited detection of $\mu_s^*$ involved a two-layered phantom. The two-layered tissue phantoms consisted of a thin superficial layer and a basal layer, as shown in FIG. 31A. The thin superficial layer was composed of a suspension of polystyrene microspheres and did not contain Hemoglobin (Hb) to mimic the epithelial layer. The basal layer consisted of a suspension of polystyrene microspheres to mimic tissue scattering and Hb to mimic light absorption in tissue. In cases where the top epithelial layer was thin, the photons contributing to the LEBS signal penetrate through the top layer into the basal layer and have a peculiar Hb absorption band at 540 nm. In other scenarios where the top layer was thick, all LEBS photons are localized in the top layer and the signal does not depict an Hb absorption band.

This methodology allowed for the experimental validation of a probe average penetration of around 116 µm. The thickness of the top layer was varied from 0 µm to 65 µm and 130 µm, without changing the basal layer. The basal layer was prepared as a solid phantom consisting of the suspension of 4.3 µm polystyrene microspheres, agarose (2%) and Human Hemoglobin. The concentrations were controlled appropriately to give ls* of 500 µm, g=0.9, [Hb]=10.4 g/L, and the thickness was controlled to 5 mm. The optical properties of the basal layer closely resemble those of human biological tissue. The thin superficial layer was made as a solid phantom slab consisting of the suspension of polystyrene microspheres of 0.87 µm (with no Hb) and the optical properties were set to be ls*=800 µm and g=0.9, mimicking the epithelial layer. The desired thickness was achieved by pouring this suspension into a mold with a spacer of particular thickness and allowing it to solidify followed by subsequent removal.

Figure 31B:
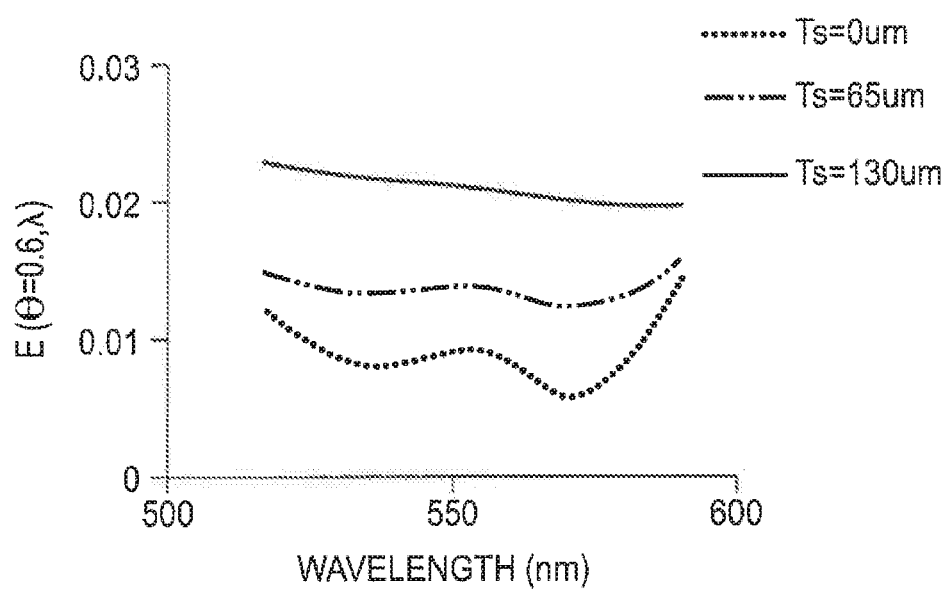
FIG. 31B shows a representative LEBS intensity spectrum for various superficial layer thicknesses.

To perform the experiments, the thin slabs were placed on a solid medium and the readings were taken from the probe placed in contact with a top layer of varying thickness. As shown in FIG. 31B, the LEBS intensity spectra at a thickness of zero (Ts=0 µm, no top layer) shows the strongest absorption band, indicating all photons traveling in the basal layer. In cases where thickness is 65 µm the absorption band is muted, followed by disappearance when the thickness is increased to 130 µm (exceeding the average penetration depth of the LEBS probe as calculated by Equation (13)). This indicates that at 130 µm almost all the photons are localized within the top layer, which highlights the depth selectivity of the probe. Thus, the geometry of an LEBS probe can be designed as described herein to achieve the desired depth selectivity of 120 µm, a depth that ex vivo data suggests is optimum for diagnostic purposes.

Figures 32A, 32B:
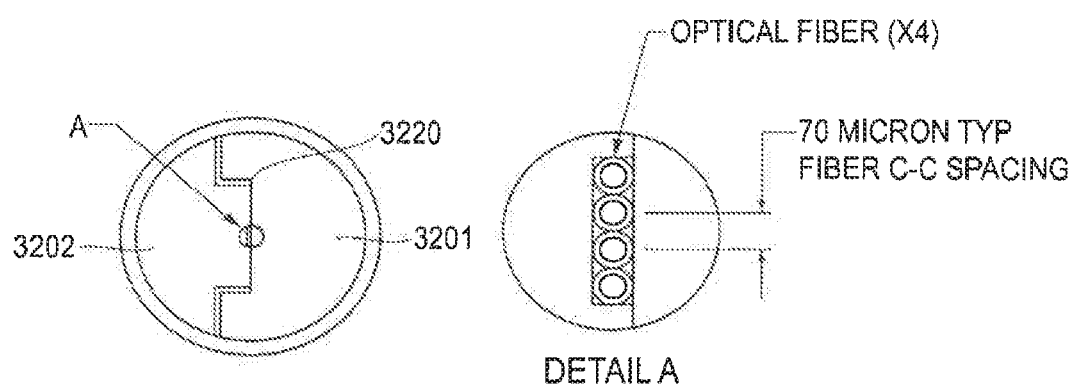
FIGS. 32A and 32B illustrate in cross section an embodiment of optical fibers usable in the optical probe assembly configurations illustrated in any of FIGS. 21-31B.

FIGS. 32A and B illustrate in cross section an embodiment of optical fibers usable in the optical probe assembly configurations illustrated in any of FIGS. 27-31. FIG. 32A shows the trunk assembly 3202, the tip assembly 3201, and the plane of the illumination fiber 3220. As shown in FIG. 32B, which is a detail of FIG. 32A taken at point A, the center-to-center spacing between fibers is ideally about 60 µm. As discussed above, in preferred embodiments using fibers having a core diameter of about 50 µm, the fiber center-to-center spacing is about 60-70 µm.

Figure 33:
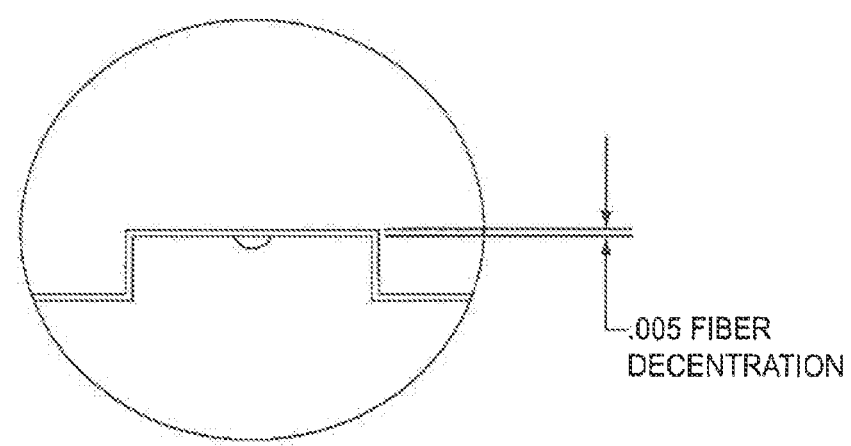
FIG. 33 illustrates in cross section a further embodiment of optical fibers usable in the optical probe assembly configurations illustrated in any of FIGS. 21-31B.

FIG. 33 illustrates in cross section a further embodiment of optical fibers usable in the optical probe assembly configurations illustrated in any of FIGS. 27-31. FIG. 33 shows a polished fiber endface of a trunk assembly, using top and bottom pieces to capture and align fibers in the desired array when the trunk assembly is assembled. The fiber assembly in FIG. 33 is decentered, i.e., the fibers are slightly asymmetric with respect to the probe center, which minimizes reflections. This technique can be used on any LEBS probe designs described herein, and advantageously causes internal reflections off surfaces (e.g. the lens/tissue interface, air/lens interface, etc.) to reflect away from the fibers. Another technique useful for preventing reflections is to employ a bevel on the end of the spacer. As discussed above, the spacer can beveled to about 4°-10°, and preferably to about 9.5°, to reduce reflections.

Figure 34A:
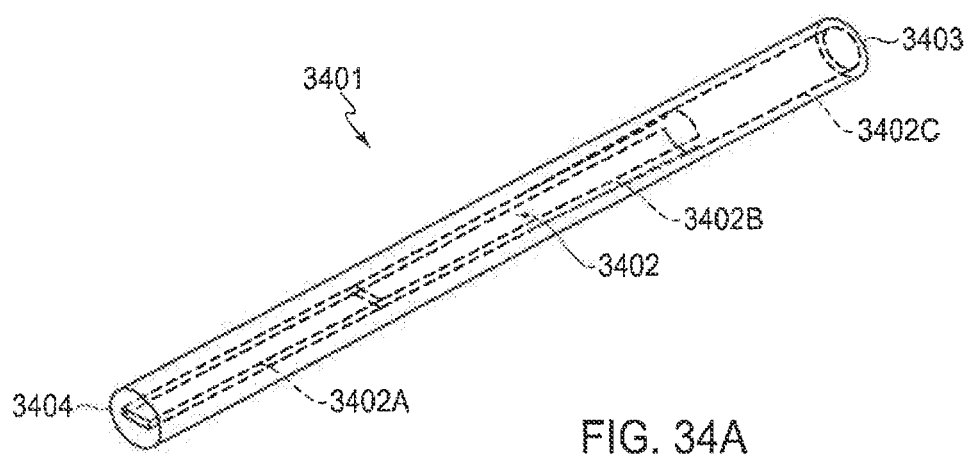
FIGS. 34A-34D illustrate a ferrule component 3401 for aligning optical fibers in a trunk assembly.
Figure 34B:
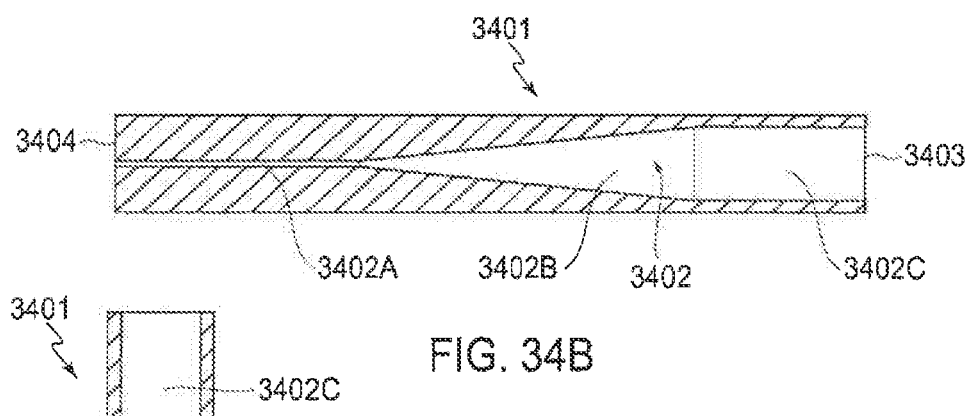
Figure 34C:
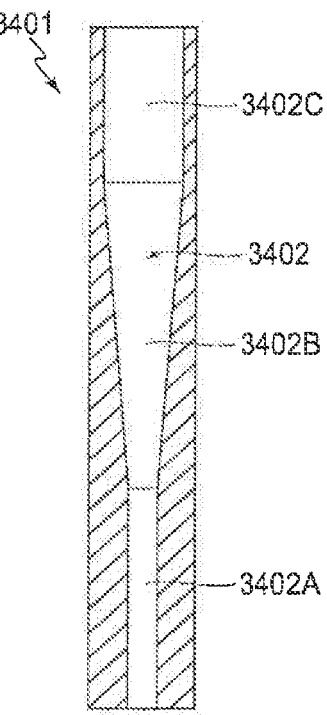
Figure 34D:
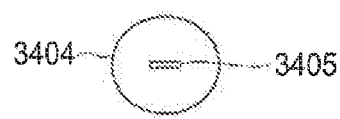

FIGS. 34A-34D illustrate a ferrule component 3401 for aligning optical fibers in a trunk assembly. The ferrule 3401, which may be manufactured from glass or other materials, such as plastic or metal, generally comprises a long cylinder with a hollowed portion 3402 etched along the axial direction. The shape of the hollowed portion changes along the axial length of the cylinder, such that the shape of region 3402c at the entry point 3403 for optic fibers cylindrical; the shape of region 3402b along the middle portion of the ferrule 3401 is generally conical, such that a circular end portion of region 3402b adjoins an end portion of region 3402c, and a rectangular end portion of region 3402b adjoins an end portion of region 3402a; and the cross-sectional shape of region 3402a is generally rectangular from the end portion that adjoins region 3402b to the end point 3404 of the optical fibers. As shown in FIGS. 34B and 34C, the cross-section of region 3402b is rectangular, and decreases in width and length from the entry point 3403 for optic fibers to the point of adjoining region 3402a, to transition from the circular cross-sectional shape of region 3403c to the rectangular cross-sectional shape of region 3403a. FIG. 34D shows a view of end point 3404, representing the endface of the ferrule, which would also be the plane of illumination in the assembled probe. The end point 3405 of region 3402a is shaped to align optical fibers in the desired alignment. Although the shape of the hollowed portion 3402 in this embodiment is described in terms of three regions, the hollowed portion can be shaped in any manner to receive the optical fibers at entry point 3403, and guide the optical fibers along the length of the ferrule into the desired array configuration at end point 3404. For example, the hollowed portion of the ferrule could be entirely conical, which may be useful if the fiber array is circular. As another example, the hollowed portion could also have a rectangular cross-section along the entire length.

FIGS. 35A-35C and 36A-36C illustrate preferred embodiments of a lens-based and a lens-free LEBS probe, respectively. The lens-based LEBS probe depicted in FIGS. 35A-35C comprises a trunk assembly 3501 connected to a tip assembly 3502. The trunk assembly 3501 comprises ferrule 3504, ferrule adapter 3504a, and tubing that may be manufactured from, for example, a polymer such as Hytrel® polyester elastomer. Ferrule 3504 is shaped as described with respect to FIGS. 34A-34D, to receive fiber assembly 3503 and align the fiber assembly end 3506 in a collinear array as described elsewhere in this application. FIG. 35A is a cross-sectional view of the embodiment rotated 90 degrees relative to the cross-sectional view shown in FIG. 35B. Together, FIGS. 35A and 35B show the rectangular cross-section of the hollowed portion of ferrule 3504, which is used to precisely align the fiber assembly 3503. Ferrule adapter 3504a is seated in the trunk assembly 3501, and aligns ferrule 3504 in the trunk assembly 3501. Ferrule adapter 3504a extends beyond the tubing of the trunk assembly 3501 to connect the trunk assembly 3501 to the tip assembly 3502. Ferrule 3504 and ferrule adapter 3504a may be comprised of the same material, such as glass, or different materials, such as plastic or metal. Tip assembly 3502 comprises a cylindrical sleeve adapted on one end to connect to the ferrule adapter 3504a, and adapted on an opposite end to house lens 3505. Lens 3505 may be, for example, a 3 mm lens. The spatial coherence length of the probe, and thus the measurement depth of the probe, is set based on the length between the fiber assembly end point 3506 and lens 3505, based on the principles described elsewhere in this application. FIG. 35C shows the fiber assembly end point 3506 when the fiber assembly 3503 is inserted into ferrule 3504. Preferably, the polyimide coating of the fibers is removed from the portion of the fibers inside ferrule 3504 when the trunk assembly is fully assembled in order to achieve desired fiber center to center spacing. In order to relieve stresses on fibers, a jacketing or "up-buffered" material such as acrylate may be used, extending at least to the inside of rear face of ferrule 3504.

The lens-free LEBS probe depicted in FIGS. 36A-36C comprises a tip assembly 3602 with an optical spacer 3605, such as a glass rod. The distal tip 3605a of the optical spacer 3605 is beveled to about 9.5°, and ideally 9.5°±0°-1°, to reduce specular reflections. The bevel is clocked to the linear fiber array such that such that fibers are symmetric to the angle of spacer bevel in order to minimize asymmetry of collection of reflected light. The spatial coherence length of the probe, and thus the measurement depth of the probe, is set based on the length of the optical spacer 3605, based on the principles described elsewhere in this application. All optical path bonds are made via index matched material to minimize internal specular reflections.

Figure 37:
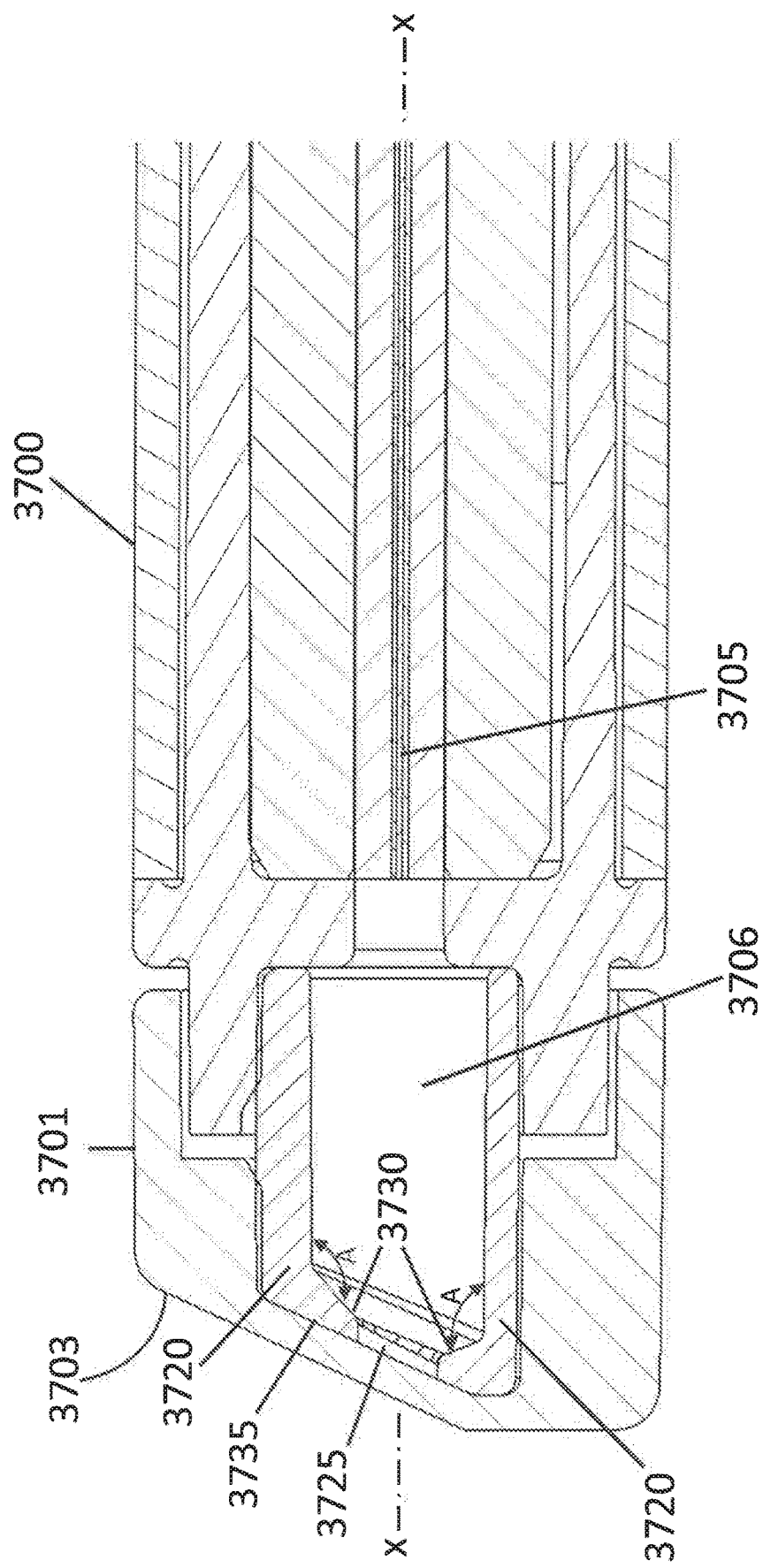
FIG. 37 illustrates an embodiment of a lens-free LEBS probe with a mask.

Referring to FIG. 37, in some embodiments it may be preferable for a tip assembly 3701 to incorporate a mask 3720 disposed at a distance distal to the endfaces of the fibers 3705 to better optimize creation and collection of the LEBS signal. The mask 3720 reduces the effective numerical aperture (NA) of the illumination and detection fibers 3705 by causing them to project to the same surface area on the target tissue. In the embodiment illustrated in FIG. 37, the mask 3720 includes a straight portion formed of a substantially cylindrical bore having an inner diameter of approximately 2.0 mm and length of approximately 3.37 mm. An optical spacer 3706 can be disposed within the substantially cylindrical bore of the straight portion of the mask 3720. The straight portion transitions to an angled portion 3730 formed of an annular surface disposed at angles A varying between approximately 110 and 140 degrees relative to the inner bore of the straight portion. Relative to the axis x-x, the angled portion forms an angle varying between approximately 40 and 70 degrees. The angled portion terminates in an opening 3725 approximately 1 mm in diameter. A distal face 3735 of the mask 3720 provides a surface angled approximately 65 degrees relative to axis x-x. Adjacent to the mask 3720's distal face 3735 is a transparent cover 3703.

To block the transmission of light, the mask, or at-least the angled portion 3730, should be made of opaque material permitting transmission of light only through the opening 3725. While the embodiment of FIG. 37 is lens-free, the mask 3720 may be adapted for use in any lens-based embodiment under a similar arrangement based on the principals discussed here.

FIGS. 38-41 illustrate some of the principles associated with the mask where certain effects are exaggerated for illustrative purposes. In particular, FIG. 38A illustrates an unmasked tip assembly 3800 with fibers 3805 projecting to target areas (shown in FIG. 38B) offset from each other. Under such an arrangement the projected illumination area differs slightly than that of the detection area potentially leading to inaccuracies. FIGS. 39A, B respectively illustrate a masked tip assembly. By blocking light disposed along the periphery, the mask 3820 aims to substantially eliminate the offset.

Figure 40:
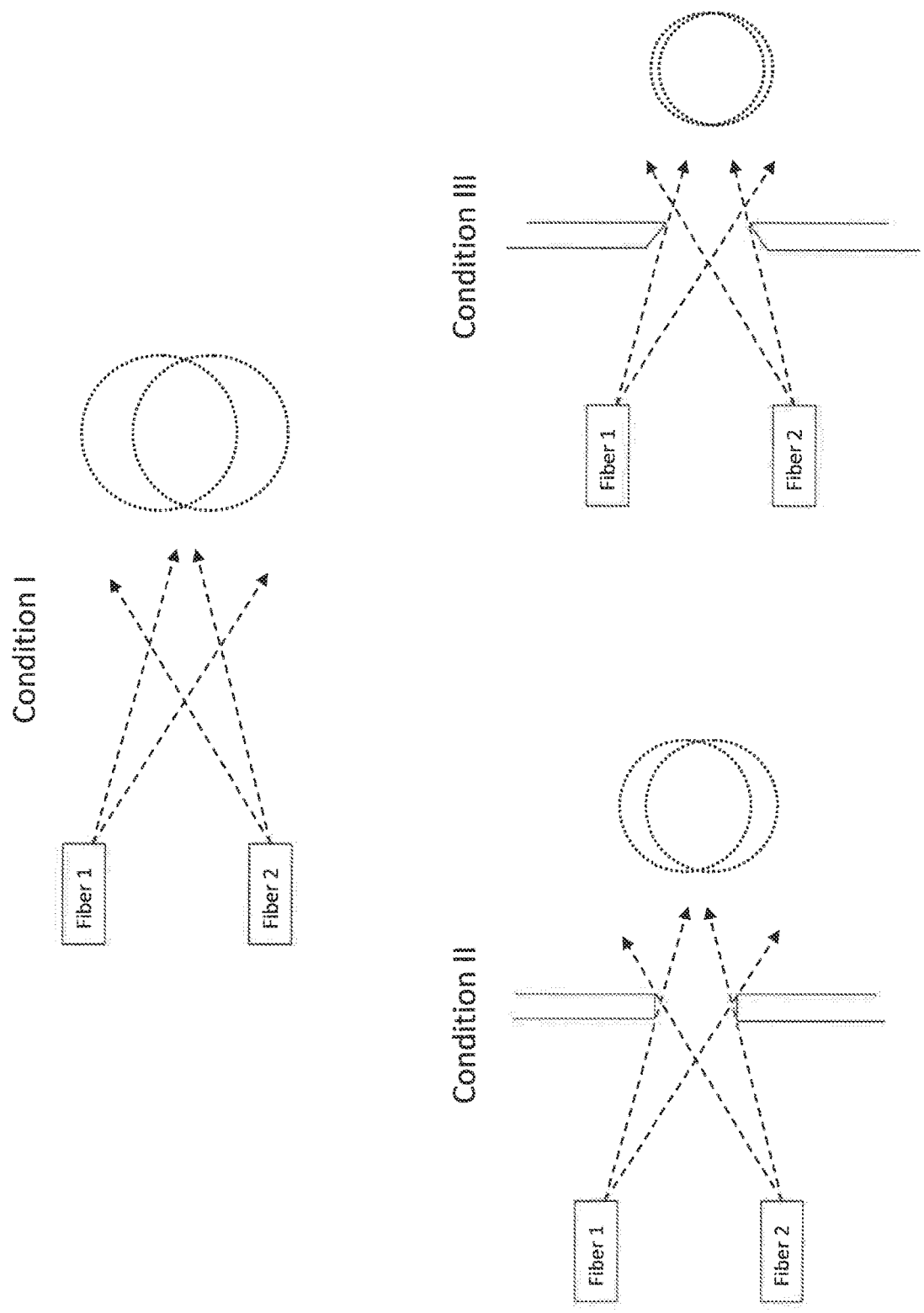
FIG. 40 illustrates concepts associated with using an angled mask.

FIG. 40 illustrates concepts associated with an angled mask. Three conditions are depicted: Condition I—no mask, Condition II—squared mask, and Condition III—angled mask. In Condition I, the projections are substantially offset. The squared mask of Condition II represents an improvement over Condition I, as the offset has been reduced. Because the light from different illumination fibers is cut by different mask corners, desired overlapping is not fully optimized. The presence of separate projections only slightly offset from each other, such as in Condition II, sometimes appears as, and is referred to as, "shadowing."

Figure 41:
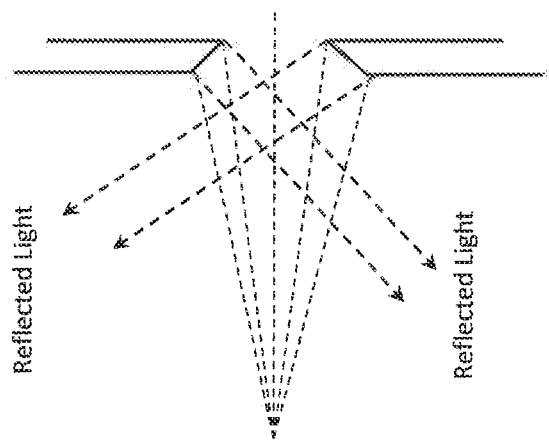
FIG. 41 illustrates light reflection paths in an angled mask embodiment.

Condition III depicts a mask having an angled portion. The projections are reduced in size compared to Conditions I and II, but with reduction of the offset further optimized. Because the projected light from each fiber is cut by a sharp edge, projections are brought close together resulting in a sharper cut of light and improved "crispness." FIG. 41 illustrates how the angled portion may also cause reflected light to deflect away from the detection fiber to reduce inaccuracies.

An appropriately arranged angled surface and mask thickness will result in ensuring all fibers, even if disposed at distances relative to each other, nevertheless collect from and illuminate a common target area (with minimal offset) that extends approximately the entirety of the opening of the mask.

The foregoing description of the exemplary embodiments of the invention has been presented only for the purposes of illustration and description and is not intended to be exhaustive or to limit the invention to the precise forms disclosed. Many modifications and variations are possible in light of the above teachings.

What is claimed is:

1. A method for performing depth-limited measurement of optical properties of a target tissue through low-coherence enhanced backscattering spectroscopy comprising:

illuminating the target tissue with broadband light emitted from a distal end of an illumination fiber housed at least in part in an optical probe, wherein the optical path of the broadband light from the illumination fiber to the target tissue passes through a mask housed, in whole or in part, in a tip assembly of the optical probe such that the mask is disposed at a distance from the distal end of the illumination fiber, a penetration depth of the broadband light into the target tissue being determined by a length of the mask; and detecting backscattered light at a plurality of backscattering angles with a plurality of detection fibers, wherein a first detection fiber detects an incoherent baseline of the backscattered light, and at least a second detection fiber detects backscattering angles within an enhanced backscattered cone.

2. The method of claim 1, wherein the optical path of the broadband light is aligned with an axis of the probe, and wherein an inner surface of the mask is disposed at an angle of between 40 and 70 degrees relative to the axis of the probe.

3. A low-coherence enhanced backscattering probe comprising:

a fiber optic array comprising an illumination fiber configured to illuminate a target tissue with broadband light emitted from a distal end of the illumination fiber;

a first detection fiber configured to detect an incoherent baseline of backscattered light;

at least a second detection fiber configured to detect backscattering angles within an enhanced backscattered cone;

a tip assembly and a mask housed, in whole or in part, in a tip assembly of the probe such that the mask is disposed at a distance from the distal end of the illumination fiber, an optical path of the broadband light from the illumination fiber to the target tissue passing through the mask, a penetration depth of the broadband light into the target tissue being determined by a length of the mask.

4. The probe of claim 3, wherein the optical path of the broadband light is aligned with an axis of the probe, and wherein an inner surface of the mask is disposed at an angle of between 40 and 70 degrees relative to the axis of the probe.

5. The probe of claim 3, wherein the mask includes a straight portion defining a substantially cylindrical bore, and an angled portion defining an opening disposed at an angle relative to the substantially cylindrical core.

6. The probe of claim 5, wherein the opening defined by the angled portion has a diameter that is less than a diameter of the substantially cylindrical bore defined by the straight portion, such that an inner surface of the angled portion overlaps with the substantially cylindrical bore.

7. The probe of claim 6, wherein the diameter of the opening is about 1.0 millimeter, and wherein the diameter of the substantially cylindrical bore is about 2.0 millimeters.

8. The probe of claim 6, wherein at least a portion of the broadband light emitted from the distal end of the illumination fiber is blocked from passing through the opening by the inner surface of the angled end portion.

9. The probe of claim 3, wherein at least a portion of the mask comprises an opaque material.

10. The probe of claim 3, wherein the mask is configured to reduce an effective numerical aperture of (i) the illumination fiber, (ii) the first detection fiber, (iii) the second detection fiber, or (iv) any combination of (i), (ii), and (iii).

11. The probe of claim 3, wherein the mask is configured to align (i) an illumination projection area of the illumination fiber and (ii) a detection projection area of the first detection fiber and the second detection fiber.

12. The method of claim 1, wherein the mask includes a straight portion defining a substantially cylindrical bore, and an angled portion defining an opening disposed at an angle relative to the substantially cylindrical core.

13. The method of claim 12, wherein the opening defined by the angled portion has a diameter that is less than a diameter of the substantially cylindrical bore defined by the straight portion, such that an inner surface of the angled portion overlaps with the substantially cylindrical bore.

14. The method of claim 13, wherein the diameter of the opening is about 1.0 millimeter, and wherein the diameter of the substantially cylindrical bore is about 2.0 millimeters.

15. The method of claim 13, wherein at least a portion of the broadband light emitted from the distal end of the illumination fiber is blocked from passing through the opening by the inner surface of the angled end portion.

16. The method of claim 1, wherein at least a portion of the mask comprises an opaque material.

17. The method of claim 1, wherein the mask reduces an effective numerical aperture of (i) the illumination fiber, (ii) the first detection fiber, (iii) the second detection fiber, or (iv) any combination of (i), (ii), and (iii).

18. The method of claim 1, wherein the mask is configured to align (i) an illumination projection area of the illumination fiber and (ii) a detection projection area of the first detection fiber and the second detection fiber.

19. A low-coherence enhanced backscattering probe comprising:
- one or more illumination fibers configured to emit broadband light from a distal end of the one or more illumination fibers to illuminate a target tissue;
- one or more first detection fibers configured to collect at least a first portion of backscattered light from the target tissue at a distal end of the one or more first detection fibers to detect an incoherent baseline of the backscattered light;
- one or more second detection fibers configured to collect at least a second portion of the backscattered light from the target tissue at a distal end of the one or more second detection fibers to detect backscattering angles within an enhanced backscattered cone; and
- a mask positioned adjacent to the distal end of the one or more illumination fibers, the mask being configured to (i) control a penetration depth of the broadband light into the target tissue and (ii) align an illumination projection area of the one or more illumination fibers and a detection projection area of the one or more first detection fibers and the one or more second detection fibers.

* * * * *